(12) United States Patent
Wang et al.

(10) Patent No.: US 7,807,601 B2
(45) Date of Patent: *Oct. 5, 2010

(54) MIXED METAL OXIDE CATALYSTS AND PROCESSES FOR THEIR PREPARATION AND USE

(75) Inventors: Kun Wang, Bridgewater, NJ (US); James C. Vartuli, West Chester, PA (US); Wilfried J. Mortier, Princeton, NJ (US); Jihad M. Dakka, Whitehouse Station, NJ (US); Robert C. Lemon, Easton, PA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 333 days.

This patent is subject to a terminal disclaimer.

(21) Appl. No.: 11/998,778

(22) Filed: Nov. 30, 2007

(65) Prior Publication Data

US 2008/0161602 A1 Jul. 3, 2008

Related U.S. Application Data

(60) Provisional application No. 60/877,270, filed on Dec. 27, 2006.

(51) Int. Cl.
*B01J 37/00* (2006.01)
*B01J 23/00* (2006.01)
(52) U.S. Cl. ..................................... 502/312; 502/104
(58) Field of Classification Search .................. 502/104, 502/312

See application file for complete search history.

(56) References Cited

U.S. PATENT DOCUMENTS

| 5,380,933 | A | 1/1995 | Ushikubo et al. |
| 5,994,580 | A | 11/1999 | Takahashi et al. |
| 6,642,174 | B2 | 11/2003 | Gaffney et al. |
| 6,914,150 | B2 | 7/2005 | Gaffney et al. |

(Continued)

FOREIGN PATENT DOCUMENTS

EP 0529853 * 7/1992

(Continued)

OTHER PUBLICATIONS

M. M. Lin, "Selective oxidation of propane to acrylic acid with molecular oxygen" Applied Catalysis A: General 207 (2001) pp. 1-16.

(Continued)

*Primary Examiner*—Taylor Victor Oh
(74) *Attorney, Agent, or Firm*—Robert A. Migliorini

(57) ABSTRACT

A catalyst for the oxidation of an alkane, alkene or mixtures thereof. The catalyst includes a mixed-metal oxide having the formula $Mo_aV_bNb_cTe_dSb_eO_f$ wherein, when a=1, b=0.01 to 1.0, c=0.01 to 1.0, d=0.01 to 1.0, e=0.01 to 1.0, and f is dependent upon the oxidation state of the other elements, the catalyst further characterized by having at least two crystal phases, the first crystal phase being an orthorhombic M1 phase and the second crystal phase being a pseudo-hexagonal M2 phase, the orthorhombic M1 phase present in an amount between greater than 60 weight percent to less than 90 weight percent. The catalysts disclosed herein exhibit a chemisorption of $NH_3$ of less than about 0.2 mmole per gram of metal oxide.

19 Claims, 13 Drawing Sheets

U.S. PATENT DOCUMENTS

| | | |
|---|---|---|
| 7,009,075 B2 | 3/2006 | Hazin |
| 7,019,169 B2 | 3/2006 | Borgmeier et al. |
| 2009/0042723 A1* | 2/2009 | Wang et al. .................. 502/312 |

FOREIGN PATENT DOCUMENTS

| | | |
|---|---|---|
| EP | 0 962 253 A2 | 8/1999 |
| EP | 1 090 684 A1 | 11/2001 |

OTHER PUBLICATIONS

M. M. Lin, "Complex metal-oxide catalysts for selective oxidation of propane and derivatives I. Catalysts preparation and application in propane selective oxidation to acrylic acid" Applied Catalysis A: General 250 (2003) pp. 305-318.

M. M. Lin, "Complex metal oxide catalysts for selective oxidation of propane and derivatives II. The relationship among catalyst preparation, structure and catalytic properties" Applied Catalysis A: General 250 (2003) pp. 287-303.

E. K. Novakova et al., "Propane Oxidation on Mo-V-Sb-Nb Mixed-Oxide Catalysts I. Kinetic and Mechanistic Studies" Journal of Catalysis 211, (2002) pp. 226-234.

E. K. Novakova et al., "Propane Oxidation on Mo-V-Sb-Nb Mixed Oxide Catalysts 2. Influence of Catalyst Activation Methods on the Reaction Mechanism" Journal of Catalysis 211, (2002) pp. 235-243.

J. N. Al-Saeedi et al., "Bulk structure and catalytic properties of mixed Mo-V-Sb-Nb oxides for selective propane oxidation to acrylic acid" Journal of Catalysis 215 (2003) pp. 108-115.

R. K. Grasselli et al., "Active centers in Mo-V-Nb-Te-Ox (amm) oxidation catalysts" Catalysis Today 91-92 (2004) pp. 251-258.

J. M. Oliver et al., Selective oxidation and ammoxidation of propane on a Mo-V-Te-Nb-O mixed metal oxide catalyst: a comparative study, Catalysis Today 96 (2004) pp. 241-249.

* cited by examiner

MIXED METAL OXIDE CATALYSTS AND PROCESSES FOR THEIR PREPARATION AND USE

This application claims the benefit of U.S. Provisional application 60/877,270 filed Dec. 27, 2006.

FIELD

Disclosed herein are mixed-metal oxide catalysts. More particularly, disclosed herein are mixed-metal oxide catalysts and processes for preparing mixed metal oxide catalysts for use in the conversion of alkanes, alkenes or mixtures thereof.

BACKGROUND

Carboxylic acids such as acetic acid, acrylic acid, and methacrylic acid are important intermediates/feedstocks for the chemical industry. For example, acrylic acid and its derivatives are perhaps the most versatile monomers for providing performance characteristics to thousands of polymer formulations, such as adhesives, adsorbents, paints, polishes, protective coatings, and sealants, to name a few.

The production of unsaturated carboxylic acids by oxidation of an olefin is well known in the art. Acrylic acid, for instance, may be commercially manufactured by the gas phase oxidation of propylene. It is also known that unsaturated carboxylic acids may also be prepared by oxidation of alkanes. For instance, acrylic acid may be prepared by the oxidation of propane.

Acrylic acid is currently produced from propylene by the gas-phase heterogeneous oxidation of propylene. The process contains two stages; the first stage requires the oxidation of propylene to acrolein using mixed metal oxides, such as Mo—Bi—Fe—W—Co—Si—K—$O_n$. The yield from this step is generally greater than 96%. The second stage requires the oxidation of acrolein to acrylic acid; a step that proceeds at a much lower temperature than the first stage. The catalyst employed in the second stage is Mo—V—W—Cu—Sb—$O_n$. The yield from this step is generally 99%. While clearly an efficient process, with rising crude oil prices, the cost of propylene has reached record levels, severely impacting the cost of this gas-phase oxidation process. As may be appreciated, a process for the production of acrylic acid by the oxidation of propane can potentially yield significant savings in manufacturing costs.

Acrylic acid is also one of the fastest growing commodity chemicals, with projected annual growth rate of about 4%; thereby requiring, on average, a new world-scale plant every year to keep up with demand. With current worldwide demand at about 3.4 million tons a year, the cost savings alone by using less expensive feed propane has the potential to revolutionize the industry. However, a suitable process for the oxidation of alkanes to unsaturated carboxylic acids that is commercially viable has yet to be achieved.

From both an economic and technological point-of-view, the cost of manufacturing acrylic acid is difficult to reduce. Moreover, the high growth rate in polypropylene usage has caused concern around the world that a propylene shortage may occur in the future, further driving up the cost of propylene. As such, significant research efforts have been aimed at developing new technologies that employ propane.

One impediment to the production of a commercially viable process for the catalytic oxidation of an alkane to an unsaturated acid is the identification of a catalyst having adequate conversion and suitable selectivity, thereby providing sufficient yield of the unsaturated acid end-product.

Candidate catalyst systems for propane oxidation to acrylic acid have included vanadium pyrophosphate (VPO) type catalysts, which have been used successfully in the industrial process for n-butane oxidation to maleic anhydride. Another is the class of heteropoly acids and their salts. The third is the multi-component mixed metal oxides, which, as indicated above, have been utilized in propylene oxidation to acrylic acid. Mixed metal oxides containing MoVTeNb have been proposed in various patents for propane oxidation. One such catalyst for use in the oxidation of propane to acrylic acid is said to be a mixed metal oxide catalysts of Mo—V—Te—Nb—O.

Nitriles, such as acrylonitrile and methacrylonitrile, have been industrially produced as intermediates for the preparation of fibers, synthetic resins, synthetic rubbers, and the like. The most popular method for producing such nitrites is to subject an alkene such as propene or isobutene to a gas phase catalytic reaction with ammonia and oxygen in the presence of a catalyst at a high temperature. Catalysts proposed for conducting this reaction include Mo—Bi—P—O catalysts, V—Sb—O catalysts, Sb—U—V—Ni—O catalysts, Sb—Sn—O catalysts, V—Sb—W—P—O catalysts and catalysts obtained by mechanically mixing a V—Sb—W—O oxide and a Bi—Ce—Mo—W—O oxide. In view of prevailing prices, attention has been directed to the development of a method for producing acrylonitrile or methacrylonitrile by an ammoxidation reaction, wherein a lower alkane, such as propane or isobutane, is used as a starting material and catalytically reacted with ammonia and oxygen in a gaseous phase in the presence of a catalyst.

U.S. Pat. No. 5,380,933 proposes a method for preparing a catalyst said to be useful in the gas phase oxidation of an alkane to an unsaturated carboxylic acid. A catalyst is proposed which is said to be prepared by combining ammonium metavanadate, telluric acid and ammonium paramolybdate to obtain a uniform aqueous solution. Ammonium niobium oxalate is added and the water removed to obtain a solid catalyst precursor. It is suggested that the solid catalyst precursor can be molded into a tablet, sieved to a desired particle size and then calcined at 600° C. under a nitrogen stream to obtain a catalyst.

U.S. Pat. Nos. 6,642,174 and 6,914,150 each propose a catalyst that includes a mixed metal oxide said to be prepared by a sol-gel technique. The catalyst is said to be useful for the conversion of an alkane, or a mixture of an alkane and an alkene, to an unsaturated carboxylic acid by vapor phase oxidation, or to an unsaturated nitrile by vapor phase oxidation in the presence of ammonia.

U.S. Pat. No. 7,009,075 proposes a process for the selective conversion of alkanes to unsaturated carboxylic acids in a one-step process with a mixed metal oxide catalyst composition. The mixed metal oxide catalyst is said to have the general formula: $MoV_aNb_bTe_cSb_dMeOx$, wherein Me is said to be optional and may be one or more selected from silver, silicon, sulfur, zirconium, titanium, aluminum, copper, lithium, sodium, potassium, rubidium, cesium, gallium, phosphorus, iron, rhenium, cobalt, chromium, manganese, arsenic, indium, thallium, bismuth, germanium, tin, cerium or lanthanum. It is said that the catalyst may be prepared by the co-precipitation of metal compounds, which are calcined to form a mixed metal oxide catalyst.

U.S. Pat. No. 7,019,169 proposes a process for preparing (meth)acrylic acid by conducting a saturated hydrocarbon precursor compound through a catalyst bed whose catalysts are said to have, as the active composition, a multimetal oxide, which has a specific X-ray diffractogram and contains the elements Mo and V, at least one of the elements Te and Sb, and also at least one of the elements from the group consisting of Nb, Ta, W, Ce and Ti, wherein the catalyst bed is interrupted by at least one catalyst bed whose catalysts are said to have, as the active composition, a multimetal oxide which contains the elements Mo, Bi and Fe.

EP 0,962,253 proposes a process for preparing a multimetal oxide catalyst. The catalyst is said to be useful for the gas phase oxidation of alkanes to unsaturated aldehydes or carboxylic acids.

EP 1,090,684 proposes a catalyst said to be useful for oxidation reactions. The catalyst is said to be useful for the gas phase oxidation of alkanes, propylene, acrolein, or isopropanol to unsaturated aldehydes or carboxylic acids.

Despite these advances in the art, there is a continuing need for new catalysts and improved processes for the production of a carboxylic acid.

SUMMARY

In one aspect, provided is a catalyst for the oxidation of an alkane, alkene or mixtures thereof. The catalyst includes a mixed-metal oxide having the formula $Mo_aV_bNb_cTe_dSb_eO_f$ wherein, when a=1, b=0.01 to 1.0, c=0.01 to 1.0, d=0.01 to 1.0, e=0.01 to 1.0, and f is dependent upon the oxidation state of the other elements. The catalyst is further characterized by having at least two crystal phases, the first crystal phase being an orthorhombic M1 phase and the second crystal phase being a pseudo-hexagonal M2 phase, the orthorhombic M1 phase present in an amount between greater than 60 weight percent to less than 90 weight percent.

In another aspect, provided is a process for preparing a catalyst for the oxidation of an alkane, alkene or mixtures thereof. The process includes the steps of admixing metal compounds, at least one of which is an oxygen containing compound, and at least one solvent to form a solution, removing the solvent from the solution to obtain a catalyst precursor and calcining the catalyst precursor at a temperature from 350° C. to 850° C. under an inert atmosphere to form a mixed-metal oxide catalyst having the formula $Mo_aV_bNb_cTe_dSb_eO_f$ wherein, when a=1, b=0.01 to 1.0, c=0.01 to 1.0, d=0.01 to 1.0, e=0.01 to 1.0, and f is dependent upon the oxidation state of the other elements. The catalyst is further characterized by having at least two crystal phases, the first crystal phase being an orthorhombic M1 phase and the second crystal phase being a pseudo-hexagonal M2 phase, the orthorhombic M1 phase present in an amount between greater than 60 weight percent to less than 90 weight percent.

In a further aspect, provided is a process for the oxidation of an alkane, alkene or mixtures thereof. The process includes the step of contacting an alkane and molecular oxygen with a catalyst that includes a mixed-metal oxide having the formula $Mo_aV_bNb_cTe_dSb_eO_f$ wherein, when a=1, b=0.01 to 1.0, c=0.01 to 1.0, d=0.01 to 1.0, e=0.01 to 1.0, and f is dependent upon the oxidation state of the other elements. The catalyst is further characterized by having at least two crystal phases, the first crystal phase being an orthorhombic M1 phase and the second crystal phase being a pseudo-hexagonal M2 phase, the orthorhombic M1 phase present in an amount between greater than 60 weight percent to less than 90 weight percent.

In a yet further aspect, provided is a catalyst for the oxidation of an alkane, alkene or mixtures thereof, said catalyst comprising a mixed-metal oxide having the formula $Mo_aV_bNb_cTe_dSb_eO_f$ wherein, when a=1, b=0.01 to 1.0, c=0.01 to 1.0, d=0.01 to 1.0, e=0.01 to 1.0, and f is dependent upon the oxidation state of the other elements. The catalyst is further characterized by having a selectivity to acrylic acid production that is inversely proportional to the chemisorption of $NH_3$ per gram of metal oxide. The catalyst exhibits a chemisorption of $NH_3$ of less than about 0.2 mmole per gram of metal oxide or less than about 0.1 mmole per gram of metal oxide.

These and other features will be apparent from the detailed description taken with reference to accompanying figures.

BRIEF DESCRIPTION OF THE DRAWINGS

The catalysts and processes for their preparation and use are further explained in the description that follows with reference to the figures illustrating, by way of non-limiting examples, various forms disclosed herein, wherein.

DETAILED DESCRIPTION

Figure 1:
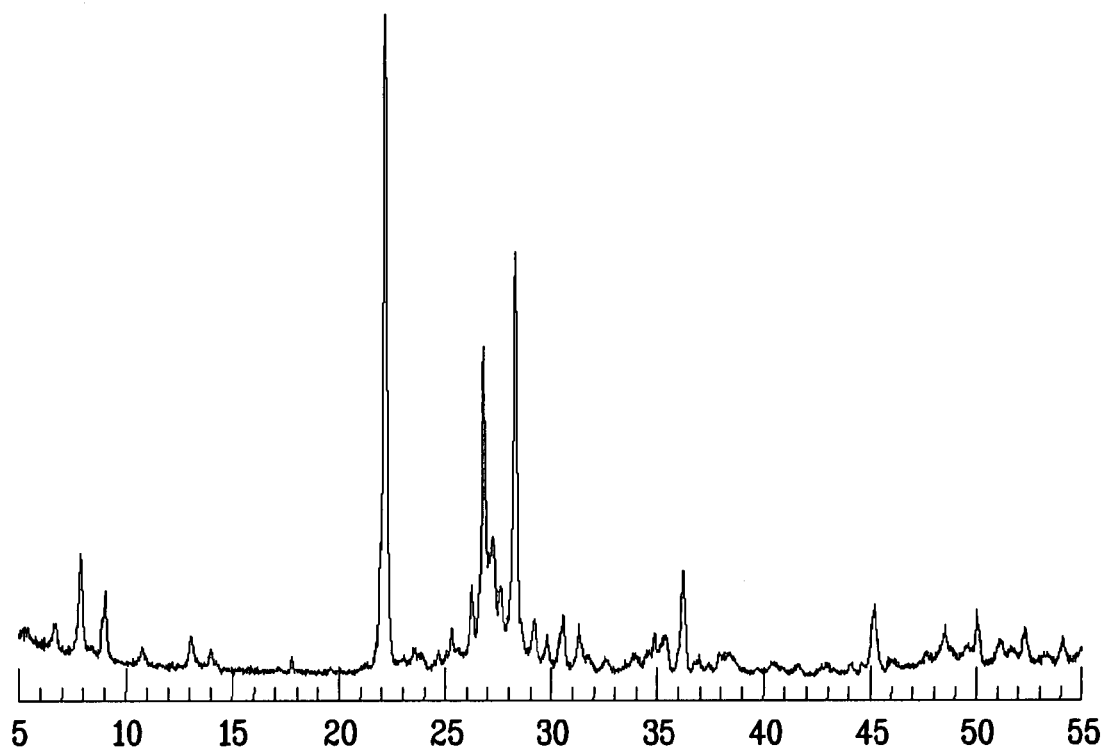
FIG. 1 is an X-ray diffraction pattern for the catalyst sample of Example 1A.

Various aspects will now be described with reference to specific forms selected for purposes of illustration. It will be appreciated that the spirit and scope of the processes and catalyst system disclosed herein is not limited to the selected forms.

As used herein the term "mixture" is meant to include within its scope all forms of mixtures including, but not limited to, simple mixtures as well as blends, alloys, etc.

As used herein by the term "solution" is meant that greater than 95 percent of a metal solid added to a solvent is dissolved.

As used herein the term "% conversion" is equal to (moles of consumed alkane/moles of supplied alkane)×100.

As used herein the term "% selectivity" is equal to (moles of formed desired unsaturated carboxylic acid/moles of consumed alkane)×100.

As used herein the term "% yield" is equal to (moles of formed desired unsaturated carboxylic acid/moles of supplied alkane)×(carbon number of formed desired unsaturated carboxylic acid/carbon number of the supplied alkane)×100.

As used herein the terminology "$(C_1-C_8)$alkane" means a straight chain or branched chain alkane having from 1 to 8 carbon atoms per alkane molecule.

As used herein the terminology "$(C_1-C_8)$alkene" means a straight chain or branched chain alkene having from 1 to 8 carbon atoms per alkene molecule.

In one form, provided is a catalyst for the oxidation of an alkane, alkene or mixtures thereof. The catalyst includes a mixed-metal oxide having the formula $Mo_aV_bNb_cTe_dSb_eO_f$ wherein, when a=1, b=0.01 to 1.0, c=0.01 to 1.0, d=0.01 to 1.0, e=0.01 to 1.0, and f is dependent upon the oxidation state of the other elements. The catalyst is further characterized by having at least two crystal phases, the first crystal phase being an orthorhombic M1 phase and the second crystal phase being a pseudo-hexagonal M2 phase, the orthorhombic M1 phase present in an amount between greater than 60 weight percent to less than 90 weight percent.

Mo—V—Te—Nb—O catalysts of the type proposed in U.S. Pat. No. 5,380,933 have been reported to contain two major crystal phases, namely an M1 phase and an M2 phase. The orthorhombic M1 phase, $Te_2M_{20}O_{57}$ (M=V, Mo, Nb), has been reported to contain both hexagonal and heptagonal channels where Te is located. The pseudo-hexagonal M2 phase, $TeM_3O_{10}$ (M=V, Mo), has been found to only posses hexagonal channels where Te is located. It is believed that the M1 phase is responsible for H-atom abstraction from propane, while the M2 phase is active for O-insertion. It has been reported that the highest acrylic acid yield is obtained for the Mo—V—Te—Nb—O catalysts of the type proposed in U.S. Pat. No. 5,380,933, when the M1 phase is in the range of 40-60 wt. %.

It has been found for the catalysts disclosed herein that the addition of a fifth metal, namely, antimony, to a mixed metal oxide system similar to the type proposed in U.S. Pat. No. 5,380,933, significantly improves catalyst performance. Nearly 50% acrylic acid yield per pass has been achieved by the catalyst systems disclosed herein. Moreover, the optimal phase composition for best acrylic acid yield, rather than being from 40-60 wt. % M1, is 70-80 wt. % M1 with the addition of Sb.

In one form, provided is a catalyst for the oxidation of an alkane, alkene or mixtures thereof, said catalyst comprising a mixed-metal oxide having the formula $Mo_aV_bNb_cTe_dSb_eO_f$ wherein, when a=1, b=0.01 to 1.0, c=0.01 to 1.0, d=0.01 to 1.0, e=0.01 to 1.0, and f is dependent upon the oxidation state of the other elements. The catalyst is further characterized by having a selectivity to acrylic acid production that is inversely proportional to the chemisorption of $NH_3$ per gram of metal oxide. As such, the catalysts disclosed herein exhibit acidity as determined by the chemisorption of $NH_3$ over these metal oxide materials.

Figure 13:
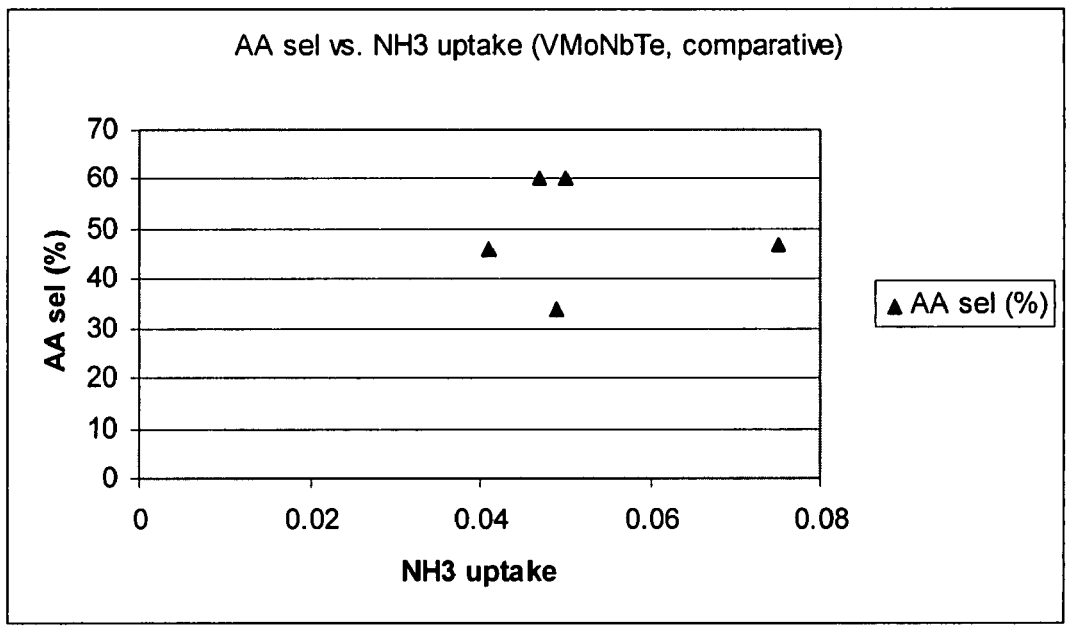
FIG. 13 is a plot of acrylic acid selectivity vs. $NH_3$ uptake for a VMoNbTe system (comparative)
Figure 14:
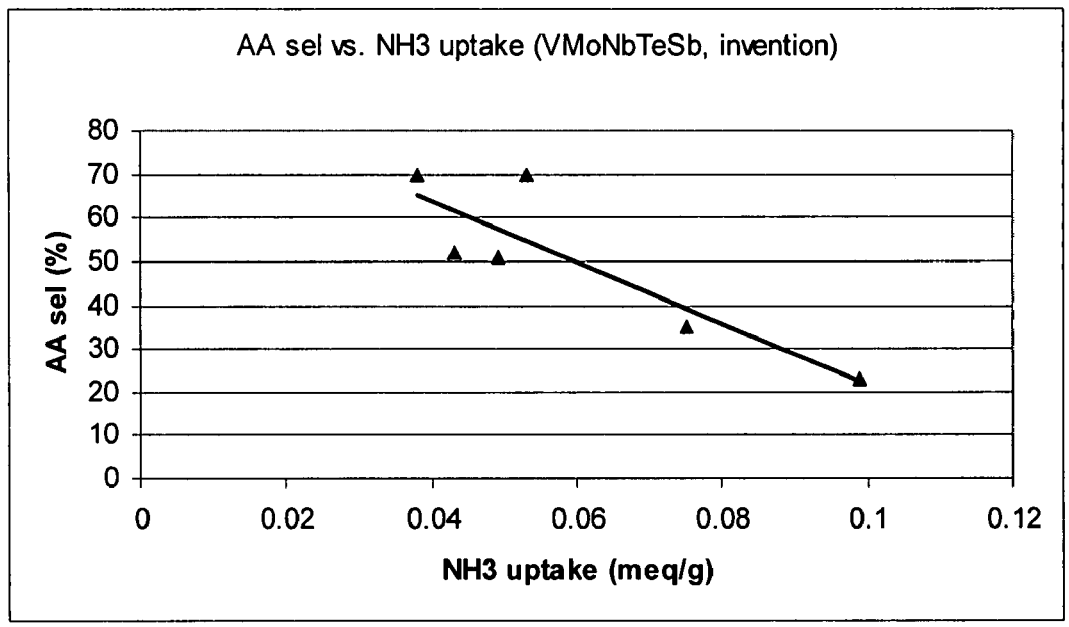
FIG. 14 is a plot of acrylic acid selectivity vs. $NH_3$ uptake for a VMoNbTeSb system.

As may be seen in Table 1 and FIGS. 13 and 14, the chemisorption of $NH_3$ per gram (mmole/g) of metal oxide for the catalysts disclosed herein was observed to be inversely proportional to the selectivity of acrylic acid production, while no such correlation was observed for any of the comparative systems. As shown in Table 1, the catalysts disclosed herein exhibited a chemisorption of $NH_3$ of less than about 0.2 mmole per gram of metal oxide or less than about 0.1 mmole per gram of metal oxide. As demonstrated below, the lower the acidity, as measured by ammonia adsorption, the more selective the catalyst.

In another form, provided is a process for preparing a catalyst for the oxidation of an alkane, alkene or mixtures thereof. The process includes the steps of admixing metal compounds, at least one of which is an oxygen containing compound, and at least one solvent to form a solution, removing the solvent from the solution to obtain a catalyst precursor and calcining the catalyst precursor at a temperature from 350° C. to 850° C. under an inert atmosphere to form a mixed-metal oxide catalyst having the formula $Mo_aV_bNb_cTe_dSb_eO_f$ wherein, when a=1, b=0.01 to 1.0, c=0.01 to 1.0, d=0.01 to 1.0, e=0.01 to 1.0, and f is dependent upon the oxidation state of the other elements. The catalyst is further characterized by having at least two crystal phases, the first crystal phase being an orthorhombic M1 phase and the second crystal phase being a pseudo-hexagonal M2 phase, the orthorhombic M1 phase present in an amount between greater than 60 weight percent to less than 90 weight percent.

The mixed metal oxide can be prepared by the following method. For example, when a mixed metal oxide of the formula $Mo_aV_bNb_cTe_dSb_eO_f$ is to be prepared, a solution or slurry of ammonium heptamolybdate, an aqueous solution of telluric acid, antimony chloride, and an aqueous solution of niobium oxalate are sequentially added to an aqueous solution containing a predetermined amount of ammonium metavanadate, so that the atomic ratio of the respective metal elements would be in the prescribed proportions, the mixture is then dried by e.g. evaporation to dryness, spray drying or vacuum drying, and finally the remaining dried product is calcined usually at a temperature of from 350° to 700° C., preferably from 400° to 650° C. usually for from 0.5 to 30 hours, preferably from 1 to 10 hours, to obtain the desired mixed metal oxide.

The above calcination treatment can be conducted in an oxygen atmosphere, although the calcination treatment may be conducted substantially in the absence of oxygen. Specifically, the treatment is carried out in an inert gas atmosphere of e.g. nitrogen, argon or helium, or in vacuo.

A wide range of materials including salts and/or oxides of molybdenum can be employed as starting materials including, for example, but not by way of limitation, ammonium heptamolybdate (($NH_4)_6Mo_7O_{24}$), molybdenum oxides (such as, for example, $MoO_3$ and $MoO_2$), molybdenum chloride ($MoCl_5$), molybdenum oxychloride ($MoOCl_4$), $Mo(OC_2H_5)_5$, molybdenum acetylacetonate ($CH_3COCH=COCH_3)_3Mo$, phosphomolybdic acid ($MoO_3 \cdot H_3PO_4$) and silicomolybdic acid ($H_4SiO_4MoO_3$). Generally, salts and/or oxides of vanadium, which can be employed include, for example, but not by way of limitation, ammonium metavanadate ($NH_4VO_3$), vanadium oxides (such as, for example, $V_2O_5$, and $V_2O_3$), vanadium oxytrichloride ($VOCl_3$), vanadium chloride ($VCl_4$), vanadium oxytriethoxide ($VO(OC_2H_5)_3$), vanadium acetylacetonate ($CH_3COCH=COCH_3)_3V$ and vanadyl acetylacetonate ($CH_3COCH=COCH_3)_2VO$. In some forms, salts and/or oxides of tellurium can be employed including, for example, but not by way of limitation, telluric acid ($Te(OH)_6$), tellurium tetrachloride ($TeCl_4$), tellurium ethoxide ($Te(OC_2H_5)_5$), tellurium isopropoxide ($Te[OCH(CH_3)_2]_4$), and tellurium dioxide ($TeO_2$). Typical salts and/or oxides of niobium which can be employed include, for example, but not by way of limitation, ammonium niobium oxalate, niobium oxide ($Nb_2O_5$), niobium chloride ($NbCl_5$), niobic acid, niobium ethoxide ($Nb(OC_2H_5)_5$) and niobium oxalate. Other oxides and salts of metals, in addition to those exemplified above, can be employed, as would be readily apparent to one of ordinary skill in the art.

A wide variety of solvents can be employed. Typical among the solvents useful are polar solvents. Such polar solvents include, for example, and not by way of limitation, water, alcohols including, for example, alkanols, such as methanol, ethanol and propanol, and diols, such as glycols, including ethylene glycol and propylene glycol. Most typical among these solvents is water. The particular form of water employed can vary, and is generally any water suitable for use in chemical synthesis including, for example, distilled water and de-ionized water. Other solvents, in addition to those exemplified above, would be readily apparent to one of ordinary skill in the art.

The amount of solvent employed in the preparation can vary and depends, for example, on the particular metal salts and/or oxides employed, the particular solvent employed, and the like. Generally speaking, the solvent is employed in an amount sufficient to place the salts and/or oxides substantially in solution, thereby avoiding or minimizing compositional and/or phase segregation. The term "substantially", as used herein in connection with solutions of metal salts and/or oxides, means that generally at least 70% of the salt and/or oxide go into solution. More generally, the solvent is employed in an amount such that at least 80% of the salt and/or oxide go into solution, preferably at least 90% being in solution or the solvent is employed in an amount such that the salts and/or oxides go completely into solution (i.e., 100% of the salt and/or oxide remains in solution).

Solvent may be removed prior to calcination. Techniques suitable for removing solvent include, for example, but not by way of limitation, vacuum drying, freeze drying, spray drying, rotary evaporation, and/or air drying. Vacuum drying can generally be performed at pressures ranging, for example, from 10 to 500 mm/Hg, and all combinations and sub-combinations of ranges and specific pressures therein. Freeze drying can typically entail freezing the gel using, for example, but not by way of limitation, liquid nitrogen, and drying the frozen material under vacuum. Spray drying can generally be performed under an inert atmosphere such as nitrogen or argon, with an inlet temperature ranging from 125° C. to 200° C. (and all combinations and sub-combinations of ranges and specific temperatures therein) and an outlet temperature ranging from 75° C. to 150° C. (and all combinations and sub-combinations of ranges and specific temperatures therein).

Rotary evaporation can generally be performed at a bath temperature ranging, for example, but not by way of limitation, from 25° C. to 90° C., and all combinations and sub-combinations of ranges and specific temperatures therein. Generally, rotary evaporation can be performed using bath temperatures of from 40° C. to 90° C., with bath temperatures of from 40° C. to 60° C. in some forms. Rotary evaporation can also generally be performed at a pressure of from 10 mm/Hg to 760 mm/Hg, and all combinations and sub-combinations of ranges and specific pressures therein. Specifically, rotary evaporation can be performed at a pressure of from 10 mm/Hg to 350 mm/Hg, with pressures of from 10 mm/Hg to 40 mm/Hg. Air drying can be conducted, for example, at temperatures ranging from 25° C. to 90° C., and all combinations and sub-combinations of ranges and specific temperatures therein.

As disclosed herein, the catalyst precursor is subjected to calcination. Calcination may be conducted in an oxidizing atmosphere, e.g., in air, oxygen-enriched air or oxygen, or in the substantial absence of oxygen, e.g., in an inert atmosphere or in vacuo. The inert atmosphere may be any material which is substantially inert, i.e., does not react or interact with, the catalyst precursor. Suitable examples include, without limitation, nitrogen, argon, xenon, helium or mixtures thereof. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 $hr^{-1}$.

The calcination is usually performed at a temperature of from 350° C. to 850° C., or from 400° C. to 700° C., or from 500° C. to 640° C. The calcination is performed for an amount of time suitable to form the aforementioned catalyst. Typically, the calcination is performed for from 0.5 to 30 hours, or from 1 to 25 hours, or from 1 to 15 hours, to obtain the desired promoted mixed metal oxide.

The calcination can be carried out in any suitable heating device, such as, for example, a furnace. Generally speaking, any type of furnace can be utilized during the heating steps. In certain forms, the heating steps can be conducted under a flow of the involved gas environment. In such forms, the heating can be conducted in a bed with continuous flow of the gas through the bed of solid catalyst particles.

A mixed metal oxide thus obtained, exhibits excellent catalytic activities by itself. However, it can be converted to a catalyst having higher activities by grinding such a mixed metal oxide.

There is no particular restriction as to the grinding method, and conventional methods may be employed. As a dry grinding method, a method of using a gas stream grinder may, for example, be mentioned wherein coarse particles are permitted to collide with one another in a high speed gas stream for grinding. The grinding may be conducted not only mechanically but also by using a mortar or the like in the case of a small scale operation.

As a wet grinding method wherein grinding is conducted in a wet state by adding water or an organic solvent to the above mixed metal oxide, a conventional method of using a rotary cylinder-type medium mill or a medium-stirring type mill, may be mentioned. The rotary cylinder-type medium mill is a wet mill of the type wherein a container for the object to be grinded, is rotated, and it includes, for example, a ball mill and a rod mill. The medium-stirring type mill is a wet mill of the type wherein the object to be grinded, contained in a container is stirred by a stirring apparatus, and it includes, for example, a rotary screw type mill, and a rotary disk type mill.

The conditions for grinding may suitably be set to meet the nature of the above-mentioned mixed metal oxide, the viscosity, the concentration, etc. of the solvent used in the case of the wet grinding, or the optimum conditions of the grinding apparatus. However, the grinding may be conducted until the average particle size of the grinded catalyst precursor would usually be at most 20 μm, more preferably at most 5 μm.

Further, in some cases, it is possible to further improve the catalytic activities by further adding a solvent to the above grinded catalyst precursor to form a solution or slurry, followed by drying again. There is no particular restriction as to the concentration of the solution or slurry, and it is usual to adjust the solution or slurry so that the total amount of the starting material compounds for the grinded catalyst precursor is from 10 to 60 wt %. Then, this solution or slurry is dried by a method such as spray drying, freeze drying, evaporation to dryness or vacuum drying, preferably by spray drying method. Further, similar drying may be conducted also in the case where wet grinding is conducted.

The oxide obtained by the above-mentioned method may be used as a final catalyst, but it may further be subjected to heat treatment usually at a temperature of from 200° to 700° C. for from 0.1 to 10 hours.

The mixed metal oxide thus obtained may be used by itself as a solid catalyst, but may be formed into a catalyst together with a suitable support such as silica, alumina, titania, aluminosilicate, diatomaceous earth or zirconia. Further, it may be molded into a suitable shape and particle size depending upon the scale or system of the reactor.

In another form, provided is a process for the oxidation of an alkane, alkene or mixtures thereof. The process includes the step of contacting an alkane and molecular oxygen with a catalyst that includes a mixed-metal oxide having the formula $Mo_aV_bNb_cTe_dSb_eO_f$ wherein, when a=1, b=0.01 to 1.0, c=0.01 to 1.0, d=0.01 to 1.0, e=0.01 to 1.0, and f is dependent upon the oxidation state of the other elements. The catalyst is further characterized by having at least two crystal phases, the first crystal phase being an orthorhombic M1 phase and the second crystal phase being a pseudo-hexagonal M2 phase, the orthorhombic M1 phase present in an amount between greater than 60 weight percent to less than 90 weight percent.

The catalysts prepared using the methods disclosed herein can be employed in various processes, particularly in processes for the oxidation of alkanes, or mixtures of alkanes and alkenes, to their corresponding unsaturated carboxylic acids. In another form, the catalysts disclosed herein can be used in the ammoxidation of alkanes, or mixtures of alkanes and alkenes, to their corresponding unsaturated nitriles.

In the production of an unsaturated carboxylic acid, the starting material gas may contain steam. In such a case, as a starting material gas to be supplied to the reaction system, a gas mixture comprising a steam-containing alkane, or a steam-containing mixture of alkane and alkene, and an oxygen-containing gas, is usually used. However, the steam-containing alkane, or the steam-containing mixture of alkane and alkene, and the oxygen-containing gas may be alternately supplied to the reaction system. The steam to be employed may be present in the form of steam gas in the reaction system, and the manner of its introduction is not particularly limited.

Further, as a diluting gas, an inert gas such as nitrogen, argon or helium may be supplied. The molar ratio (alkane or mixture of alkane and alkene):(oxygen):(diluting gas):($H_2O$) in the starting material gas may be (1):(0.1 to 10):(0 to 20):(0.2 to 70), or (1):(1 to 5.0):(0 to 10):(5 to 40).

When steam is supplied together with the alkane, or the mixture of alkane and alkene, as starting material gas, the unsaturated carboxylic acid can be obtained from the alkane, or mixture of alkane and alkene, in good yield by contacting in one stage. However, the conventional technique utilizes a diluting gas such as nitrogen, argon or helium for the purpose of diluting the starting material. As such a diluting gas, to adjust the space velocity, the oxygen partial pressure and the steam partial pressure, an inert gas such as nitrogen, argon or helium may be used together with the steam.

A $C_{1-8}$ alkane, such as propane, isobutane or n-butane may be used as the starting material alkane. As disclosed herein, from such an alkane, an unsaturated carboxylic acid such as an α,β-unsaturated carboxylic acid can be obtained. For example, when propane or isobutane is used as the starting material alkane, acrylic acid or methacrylic acid will be obtained, respectively.

As disclosed herein, with a starting material mixture of alkane and alkene, it is possible to employ a mixture of $C_{1-8}$ alkane and $C_{1-8}$ alkene, such as propane and propene, isobutane and isobutene or n-butane and n-butene. From such a mixture of an alkane and an alkene, an unsaturated carboxylic acid such as an α,β-unsaturated carboxylic acid can be obtained. For example, when propane and propene or isobutane and isobutene are used as the starting material mixture of alkane and alkene, acrylic acid or methacrylic acid will be obtained, respectively. For the mixture of alkane and alkene, the alkene is present in an amount of at least 0.5% by weight or 1.0% by weight to 95% by weight or 3% by weight to 90% by weight.

As an alternative, an alkanol, such as isobutanol, which will dehydrate under the reaction conditions to form its corresponding alkene, i.e. isobutene, may also be used as a feed to the process disclosed herein or in conjunction with the previously mentioned feed streams.

The purity of the starting material alkane is not particularly limited, and an alkane containing a lower alkane such as methane or ethane, air or carbon dioxide, as impurities, may be used. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used. Further, the starting material mixture of alkane and alkene may be a mixture of various alkanes and alkenes.

There is no limitation on the source of the alkene. It may be purchased or in admixture with an alkane and/or other impurities. Alternatively, it can be obtained as a by-product of alkane oxidation. Similarly, there is no limitation on the source of the alkane. It may be purchased or in admixture with an alkene and/or other impurities. Moreover, the alkane, regardless of source, and the alkene, regardless of source, may be blended as desired.

The oxidation reaction is carried out by oxygen atoms present in the promoted mixed metal oxide or by molecular oxygen present in the feed gas. To incorporate molecular oxygen into the feed gas, such molecular oxygen may be pure oxygen gas. However, it is usually more economical to use an oxygen-containing gas such as air.

It is also possible to use only an alkane, or a mixture of alkane and alkene, substantially in the absence of molecular oxygen for the vapor phase catalytic reaction. In such a case, a method may be employed wherein a part of the catalyst is appropriately withdrawn from the reaction zone from time to time, then sent to an oxidation regenerator, regenerated and then returned to the reaction zone for reuse. As the regeneration method of the catalyst, a method may, for example, but not by way of limitation, be one which comprises contacting an oxidative gas such as oxygen, air or nitrogen monoxide with the catalyst in the regenerator usually at a temperature of from 300° to 600° C.

These aspects will be described in further detail with respect to a case where propane is used as the starting material alkane and air is used as the oxygen source. The reaction system may be a fixed bed system or a fluidized bed system. However, since the reaction is an exothermic reaction, a fluidized bed system may be employed since it is easy to control the reaction temperature. The proportion of air to be supplied to the reaction system can be a factor for the selectivity for the resulting acrylic acid, and it is usually at most about 25 moles, or from 0.2 to 18 moles per mole of propane, whereby high selectivity for acrylic acid can be obtained. This reaction can be conducted usually under atmospheric pressure, but may be conducted under a slightly elevated pressure or slightly reduced pressure. With respect to other alkanes such as isobutane, or to mixtures of alkanes and alkenes such as propane and propene, the composition of the feed gas may be selected in accordance with the conditions for propane.

Typical reaction conditions for the oxidation of propane or isobutane to acrylic acid or methacrylic acid may be utilized in the practice of the processes disclosed herein. The process may be practiced in a single pass mode (only fresh feed is fed to the reactor) or in a recycle mode (at least a portion of the reactor effluent is returned to the reactor). General conditions for the process disclosed herein are as follows: the reaction temperature can vary from 200° C. to 700° C., but is usually in the range of from 200° C. to 550° C., or 250° C. to 480° C., or 300° C. to 400° C.; the gas space velocity, SV, in the vapor phase reaction is usually within a range of from 100 to 10,000 $hr^{-1}$, or 300 to 6,000 $hr^{-1}$, or 300 to 2,000 $hr^{-1}$; the average contact time with the catalyst can be from 0.01 to 10 seconds or more, but is usually in the range of from 0.1 to 10 seconds, or from 2 to 6 seconds; the pressure in the reaction zone usually ranges from 0 to 75 psig, but is generally no more than 50 psig. In a single pass mode process, the oxygen may be supplied from an oxygen-containing gas such as air. The single pass mode process may also be practiced with oxygen addition. In the practice of the recycle mode process, oxygen gas by itself may be used so as to avoid the build up of inert gases in the reaction zone.

In the oxidation reaction disclosed herein, it is important that the hydrocarbon and oxygen concentrations in the feed gases be maintained at the appropriate levels to minimize or avoid entering a flammable regime within the reaction zone or especially at the outlet of the reactor zone. Generally, the outlet oxygen levels are low to both minimize after-burning and, particularly, in the recycle mode of operation, to minimize the amount of oxygen in the recycled gaseous effluent stream. In addition, operation of the reaction at a low temperature (below 450° C.) is extremely attractive because after-burning becomes less of a problem which enables the attainment of higher selectivity to the desired products. The catalyst disclosed herein operates more efficiently at the lower temperature range set forth above, significantly reducing the formation of acetic acid and carbon oxides, and increasing selectivity to acrylic acid. As a diluting gas to adjust the space velocity and the oxygen partial pressure, an inert gas such as nitrogen, argon or helium may be employed.

When the oxidation reaction of propane, and especially the oxidation reaction of propane and propene, is conducted by the method disclosed herein, carbon monoxide, carbon dioxide, acetic acid, etc. may be produced as by-products, in addition to acrylic acid. Further, in the method disclosed herein, an unsaturated aldehyde may sometimes be formed depending upon the reaction conditions. For example, when propane is present in the starting material mixture, acrolein may be formed; and when isobutane is present in the starting material mixture, methacrolein may be formed. In such a case, such an unsaturated aldehyde can be converted to the desired unsaturated carboxylic acid by subjecting it again to the vapor phase catalytic oxidation with the promoted mixed metal oxide-containing catalyst disclosed herein or by subjecting it to a vapor phase catalytic oxidation reaction with a conventional oxidation reaction catalyst for an unsaturated aldehyde.

In a further aspect, provided is a process for producing an unsaturated nitrile, which comprises subjecting an alkane, or a mixture of an alkane and an alkene, to a vapor phase catalytic oxidation reaction with ammonia in the presence of a catalyst of the type disclosed herein to produce an unsaturated nitrile.

In the production of such an unsaturated nitrile, as the starting material alkane, a $C_{1-8}$ alkane such as propane, butane, isobutane, pentane, hexane and heptane may be employed. However, in view of the industrial application of nitrites to be produced, a lower alkane having 3 or 4 carbon atoms, may be employed, such as propane and isobutane.

Similarly, as the starting material mixture of alkane and alkene, it is possible to employ a mixture of $C_{1-8}$ alkane and $C_{1-8}$ alkene such as propane and propene, butane and butene, isobutane and isobutene, pentane and pentene, hexane and hexene, and heptane and heptene. However, in view of the industrial application of nitrites to be produced, a mixture of a lower alkane having 3 or 4 carbon atoms and a lower alkene having 3 or 4 carbon atoms may be employed, such as propane and propene or isobutane and isobutene. In the mixture of alkane and alkene, the alkene is present in an amount of at least 0.5% by weight, or at least 1.0% by weight to 95% by weight, or 3% by weight to 90% by weight.

The purity of the starting material alkane is not particularly limited, and an alkane containing a lower alkane such as methane or ethane, air or carbon dioxide, as impurities, may be used. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used. Further, the starting material mixture of alkane and alkene may be a mixture of various alkanes and alkenes.

There is no limitation on the source of the alkene. It may be purchased or in admixture with an alkane and/or other impurities. Alternatively, it can be obtained as a by-product of alkane oxidation. Similarly, there is no limitation on the source of the alkane. It may be purchased or in admixture with an alkene and/or other impurities. Moreover, the alkane, regardless of source, and the alkene, regardless of source, may be blended as desired.

The ammoxidation reaction is conducted by the oxygen atoms present in the promoted mixed metal oxide disclosed herein or by the molecular oxygen in the feed gas. When molecular oxygen is incorporated in the feed gas, the oxygen may be pure oxygen gas. However, since high purity is not required, it is usually economical to use an oxygen-containing gas such as air.

As the feed gas, it is possible to use a gas mixture comprising an alkane, or a mixture of an alkane and an alkene, ammonia and an oxygen-containing gas. However, a gas mixture comprising an alkane or a mixture of an alkane and an alkene and ammonia, and an oxygen-containing gas may be supplied alternately.

When the gas phase catalytic reaction is conducted using an alkane, or a mixture of an alkane and an alkene, and ammonia substantially free from molecular oxygen, as the feed gas, it is advisable to employ a method wherein a part of the catalyst is periodically withdrawn and sent to an oxidation regenerator for regeneration, and the regenerated catalyst is returned to the reaction zone. As a method for regenerating the catalyst, a method may be mentioned wherein an oxidizing gas such as oxygen, air or nitrogen monoxide is permitted to flow through the catalyst in the regenerator usually at a temperature of from 300° C. to 600° C.

These aspects will be described in further detail with respect to a case where propane is used as the starting material alkane and air is used as the oxygen source. The proportion of air to be supplied for the reaction is a factor with respect to the selectivity for the resulting acrylonitrile. High selectivity for acrylonitrile may be obtained when air is supplied within a range of at most 25 moles, or 1 to 15 moles, per mole of the propane. The proportion of ammonia to be supplied for the reaction may be within a range of from 0.2 to 5 moles, or 0.5 to 3 moles, per mole of propane. This reaction may usually be conducted under atmospheric pressure, but may be conducted under a slightly increased pressure or a slightly reduced pressure. With respect to other alkanes such as isobutane, or to mixtures of alkanes and alkenes such as propane and propene, the composition of the feed gas may be selected in accordance with the conditions for propane.

The processes of these aspects may be conducted at a temperature of, for example, from 250° C. to 480° C. or from 300° C. to 400° C. The gas space velocity, SV, in the gas phase reaction is usually within the range of from 100 to 10,000 hr$^{-1}$, or from 300 to 6,000 hr$^{-1}$, or from 300 to 2,000 hr$^{-1}$. As a diluent gas, for adjusting the space velocity and the oxygen partial pressure, an inert gas such as nitrogen, argon or helium can be employed. When ammoxidation of propane is conducted by the method disclosed herein, in addition to acrylonitrile, carbon monoxide, carbon dioxide, acetonitrile, hydrocyanic acid and acrolein may form as by-products.

As indicated, the catalysts disclosed here can also be used for the oxidation of liquefied petroleum gas ($C_2$-$C_4$ range molecules), Fischer-Tropsch light gas ($C_1$-$C_4$), and can even be employed with catalytic cracker overhead gas (containing propane and a small amount of propylene) directly to carboxylic acids without separation. Due to the abundance of these otherwise low value feeds in certain chemical plants and refineries, direct oxidation to carboxylic acids is particularly attractive.

Now, specific forms will be described in further detail with reference to the following non-limiting examples.

EXAMPLES

Example 1

Preparation of MoVNbTeOx Precursor (Comparative)

To 700 grams of distilled water, 7.5 grams of ammonium metavanadate ($NH_4VO_3$), 52 grams of ammonium heptamolybdate tetrahydrate [$(NH_4)_6Mo_7O_{24}.4H_2O$], and 20 grams of telluric acid [$Te(OH)_6$] were added with stirring. Then 18.6 grams of niobium oxalate [$Nb(HC_2O_4)_5$] were dissolved in 200 grams of distilled water and then added to the above solution. After stirring the solution for one hour, the solution is then rotovaped to dryness at 50° C. with vacuum. The dry solid thus obtained is used in Examples 1A, 1B, 1C and 1D.

Example 1A

The catalyst precursor MoVNbTeOx prepared following the procedures above was placed in a crucible and placed in a furnace. A stream of $N_2$ (50 cc/min) was flowing through the furnace and the temperature was raised to 600° C. at 2° C./min and held at 600° C. for 2 hr. The X-ray diffraction pattern for the catalyst sample thus obtained is presented in FIG. 1. The elemental analyses were: V—4.25 weight %, Nb—5.26%, Mo—44.04%, and Te—15.0%.

Example 1B

Figure 2:
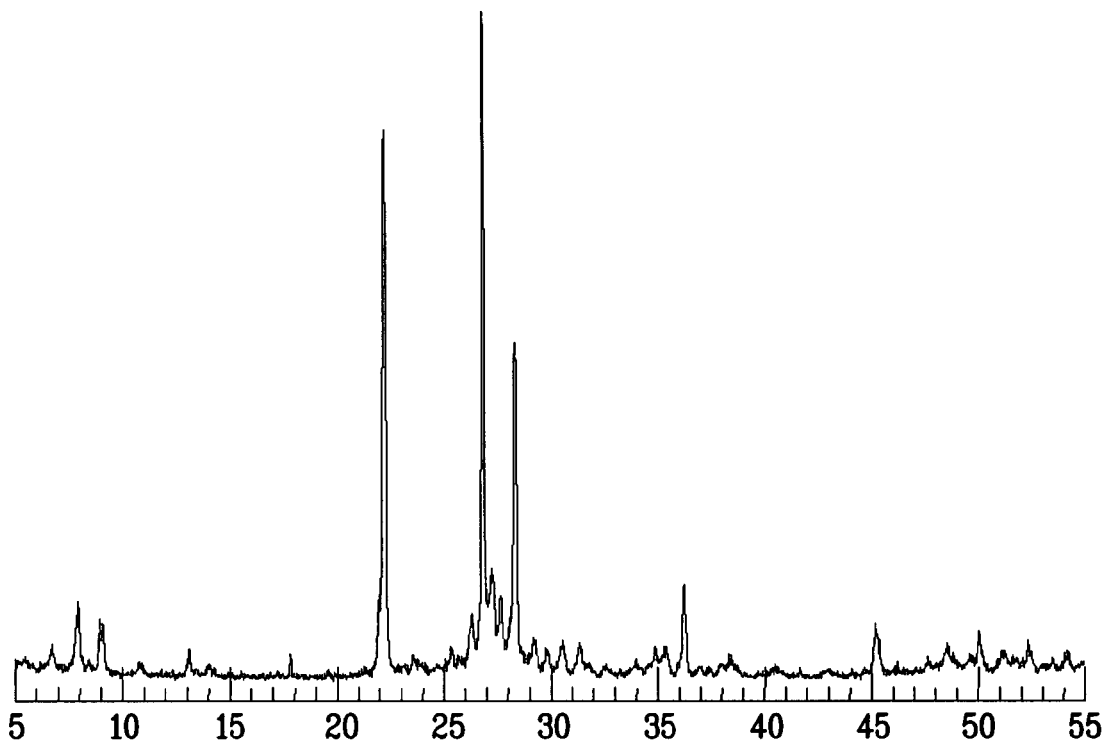
FIG. 2 is an X-ray diffraction pattern for the catalyst sample of Example 1B.

The catalyst precursor MoVNbTeOx prepared following the procedures above was placed in a crucible and placed in a furnace. A stream of $N_2$ (50 cc/min) was flowing through the furnace and the temperature was raised to 600° C. at 2° C./min and held at 600° C. for 1 hr. The X-ray diffraction pattern for the catalyst sample thus obtained is presented in FIG. 2.

Example 1C

Figure 3:
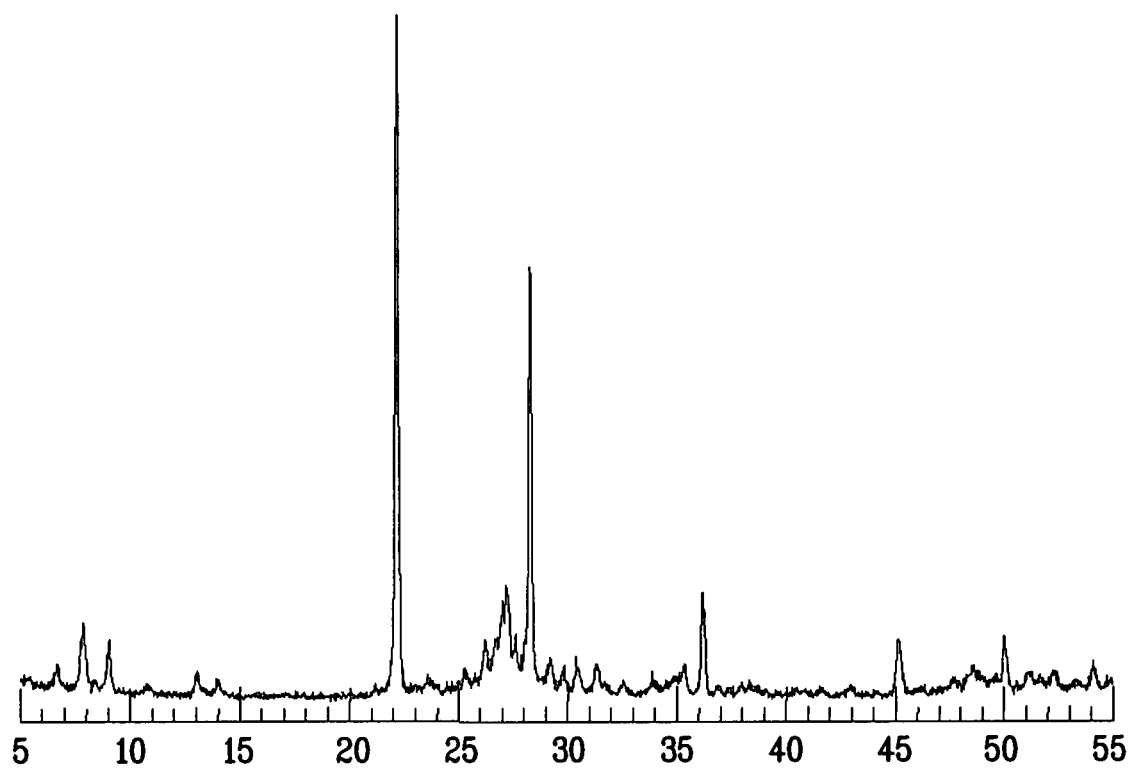
FIG. 3 is an X-ray diffraction pattern for the catalyst sample of Example 1C.

The catalyst precursor MoVNbTeOx prepared following the procedures above was placed in a crucible and placed in a furnace. A stream of He (50 cc/min) was flowing through the furnace and the temperature was raised to 600° C. at 2° C./min and held at 600° C. for 2 hr. The X-ray diffraction pattern for the catalyst sample thus obtained is presented in FIG. 3.

Example 1D

Figure 4:
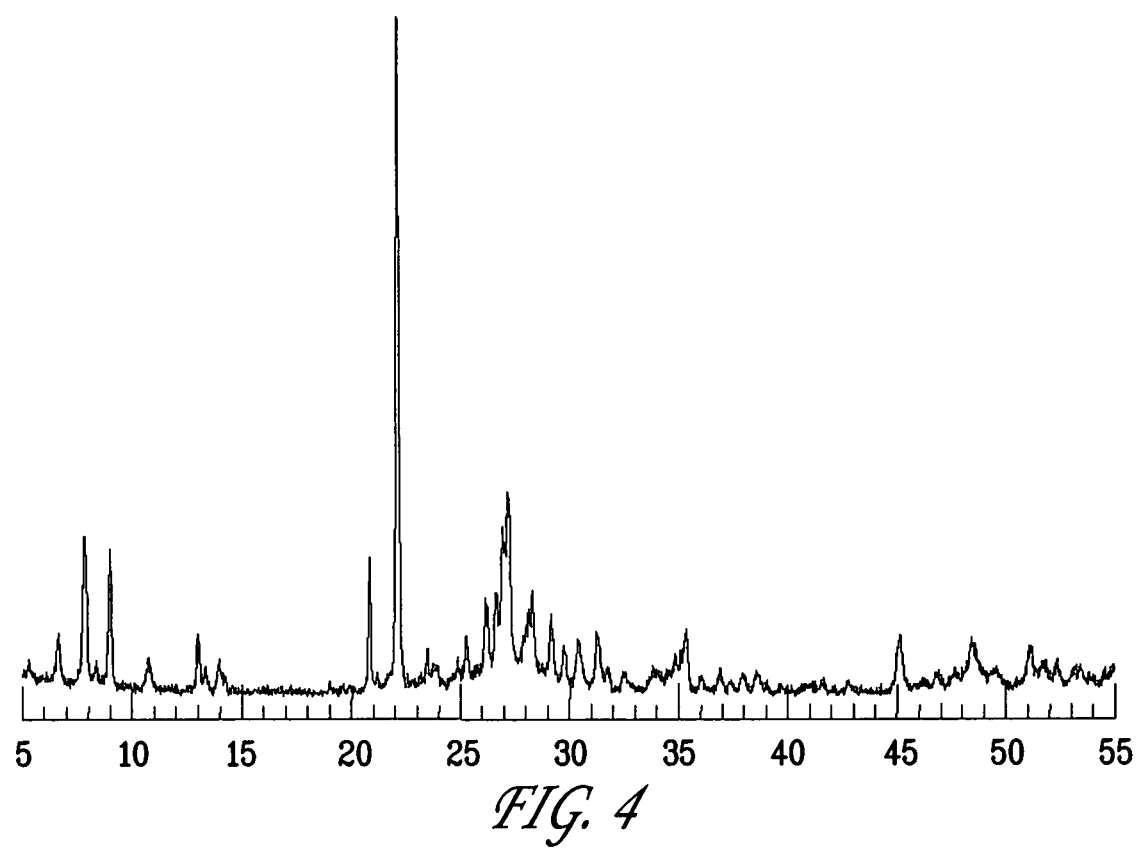
FIG. 4 is an X-ray diffraction pattern for the catalyst sample of Example 1D.

The catalyst precursor MoVNbTeOx prepared following the procedures above was placed in a crucible and placed in a furnace. A stream of $N_2$ (50 cc/min) was flowing through the furnace and the temperature was raised to 700° C. at 2° C./min and held at 700° C. for 2 hr. The X-ray diffraction pattern for the catalyst sample thus obtained is presented in FIG. 4.

Example 2

Preparation of MoVNbTeOx Catalysts (Comparative)

Figure 5:
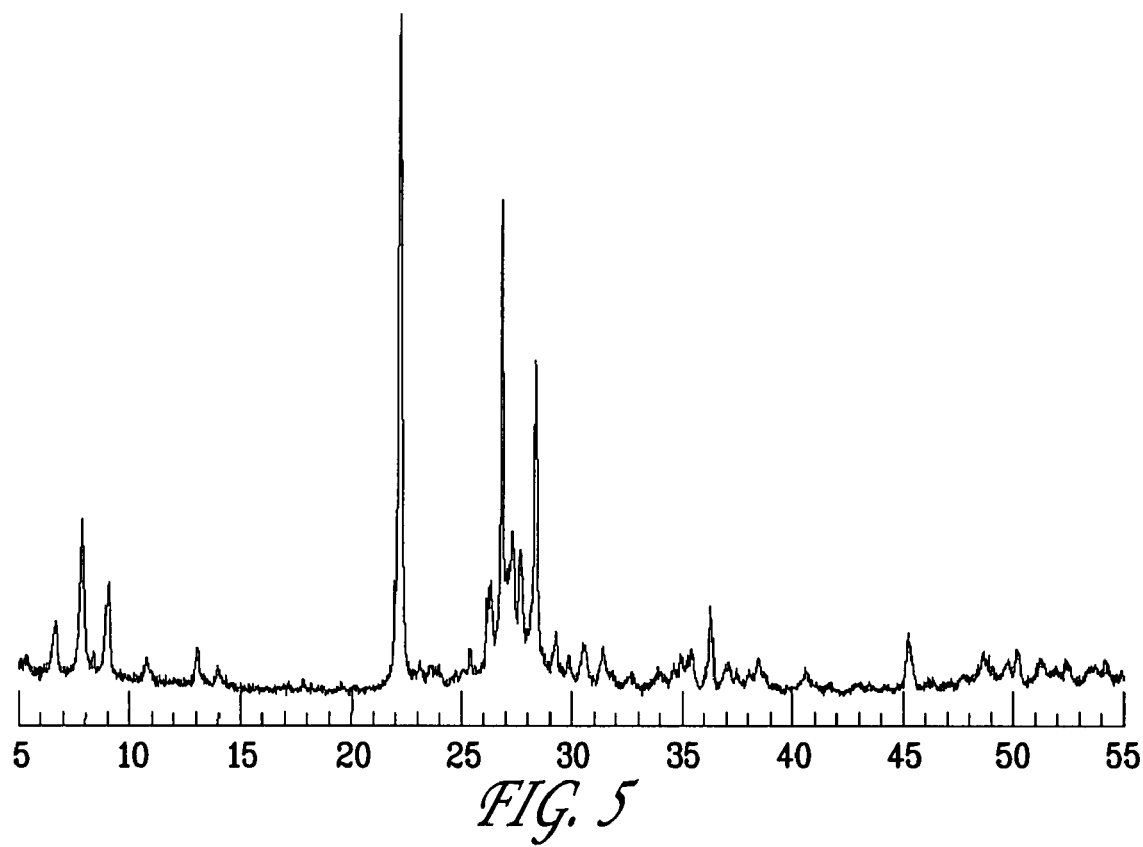
FIG. 5 is an X-ray diffraction pattern for the catalyst sample of Example 2.
Figure 6:
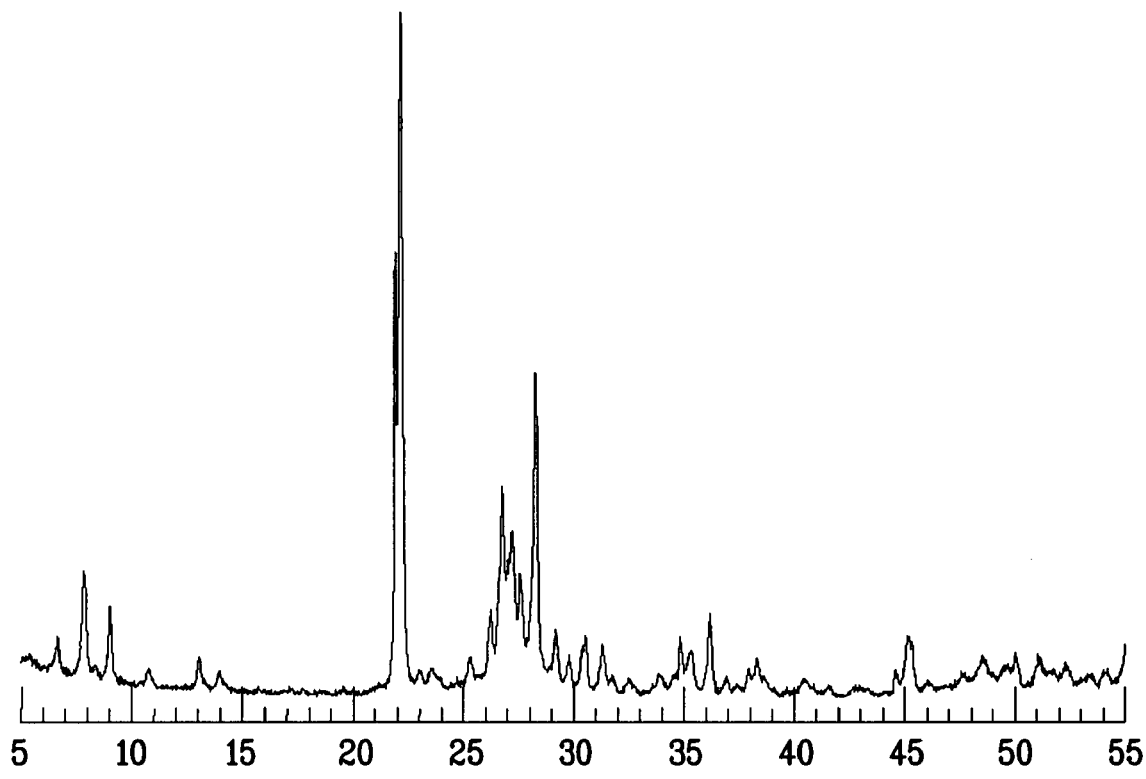
FIG. 6 is an X-ray diffraction pattern for the catalyst sample of Example 3.

To 700 grams of distilled water, 7.5 grams of ammonium metavanadate ($NH_4VO_3$), 52 grams of ammonium heptamolybdate tetrahydrate [$(NH_4)_6Mo_7O_{24}.4H_2O$] and 20 grams of telluric acid [$Te(OH)_6$] were added with stirring. Then 18.6 grams of niobium oxalate [$Nb(HC_2O_4)_5$] were dissolved in 200 grams of distilled water and then added to the above solution. After stirring the solution for one hour, the solution is then rotovaped to dryness at 50° C. with vacuum. A portion of the preparation is then calcined in flowing nitrogen at 600° C. for 2 hours. The X-ray diffraction pattern for the catalyst sample thus obtained is presented in FIG. 5). The elemental analyses were: V—4.51 weight %, Nb—5.67%, Mo—44.55%, and Te—13.1%.

Example 3

Preparation of MoVNbTeSbOx Catalysts

Figure 7:
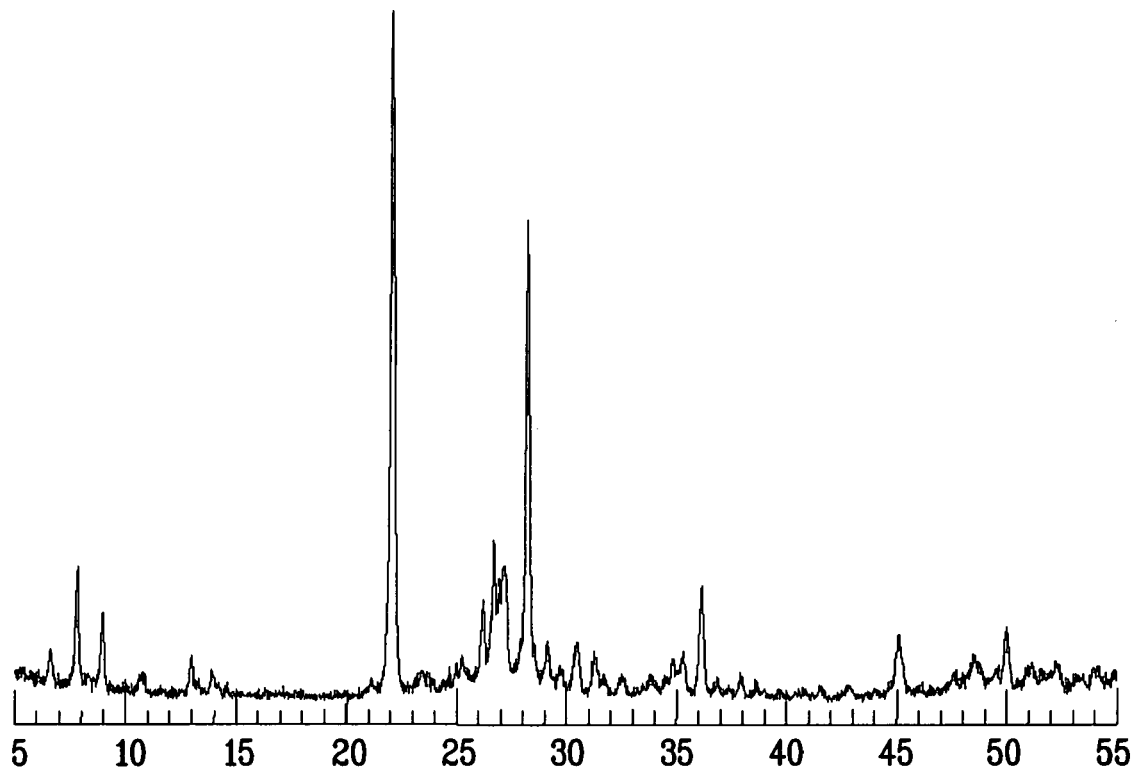
FIG. 7 is an X-ray diffraction pattern for the catalyst sample of Example 4.

To 900 grams of distilled water, 7.5 grams of ammonium metavanadate ($NH_4VO_3$), 52 grams of ammonium heptamolybdate tetrahydrate [$(NH_4)_6Mo_7O_{24}.4H_2O$], 15.5 grams of telluric acid [$Te(OH)_6$], and 4.5 grams of antimony chloride ($SbCl_3$) were added with stirring. Then 18.6 grams of niobium oxalate [$Nb(HC_2O_4)_5$] were dissolved in 200 grams of distilled water and then added to the above solution. After stirring the solution for one hour, the solution is then rotovaped to dryness at 50° C. with vacuum. A portion of the preparation is then calcined in flowing nitrogen at 600° C. for 2 hours. The X-ray diffraction pattern for the catalyst sample thus obtained is presented in FIG. 7. The elemental analyses were: V—4.7 weight %, Nb—5.55%, Mo—44.18%, Te—11.4%, and Sb—2.6%.

Example 4

Preparation of MoVNbTeSbOx Catalyst

To 900 grams of distilled water, 7.5 grams of ammonium metavanadate ($NH_4VO_3$), 52 grams of ammonium heptamolybdate tetrahydrate [$(NH_4)_6Mo_7O_{24}.4H_2O$], 15.5 grams of telluric acid [$Te(OH)_6$], and 4.5 grams of antimony chloride ($SbCl_3$) were added with stirring. Then 18.6 grams of niobium oxalate [Nb(HC$_2$O$_4$)$_5$] dissolved in 200 grams of distilled water was then added to the above solution. After stirring the solution for one hour, the solution is then rotovaped to dryness at 50° C. with vacuum. A portion of the solid isolated was placed in a crucible and placed in a furnace. A stream of Ar (50 cc/min) was flowing through the furnace and the temperature was raised to 600° C. at 2° C./min and held at 600° C. for 2 hr. The X-ray diffraction pattern for the catalyst sample thus obtained is presented in FIG. 7.

Example 5

Preparation of MoVNbTeSbOx Precursor

To 900 grams of distilled water, 7.5 grams of ammonium metavanadate (NH$_4$VO$_3$), 52 grams of ammonium heptamolybdate tetrahydrate [(NH$_4$)$_6$Mo$_7$O$_{24}$.4H$_2$O], 15.5 grams of telluric acid [Te(OH)$_6$], and 4.5 grams of antimony chloride (SbCl$_3$) were added with stirring. Then 18.6 grams of niobium oxalate [Nb(HC$_2$O$_4$)$_5$] were dissolved in 200 grams of distilled water and then added to the above solution. After stirring the solution for one hour, the solution is then rotovaped to dryness at 50° C. with vacuum. The dry solid thus obtained is used in Examples 5A and 5B.

Example 5A

Figure 8:
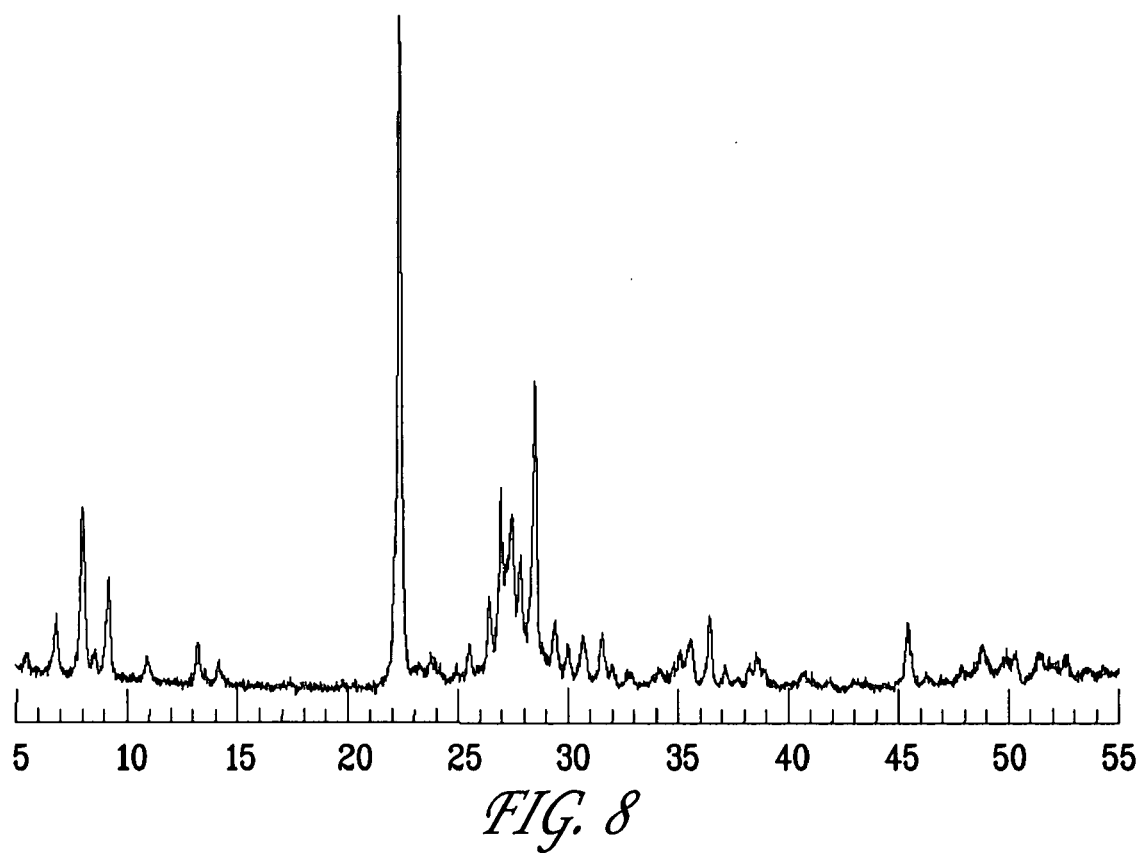
FIG. 8 is an X-ray diffraction pattern for the catalyst sample of Example 5A.

The catalyst precursor MoVNbTeSbOx prepared following the procedures above was placed in a crucible and placed in a furnace. A stream of N$_2$ (50 cc/min) was flowing through the furnace and the temperature was raised to 600° C. at 2° C./min and held at 600° C. for 2 hr. The X-ray diffraction pattern for the catalyst sample thus obtained is presented in FIG. 8. The elemental analyses were: V—4.71 weight %, Nb—6.18%, Mo—43.88%, Te—10.7%, and Sb—2.9%.

Example 5B

Figure 9:
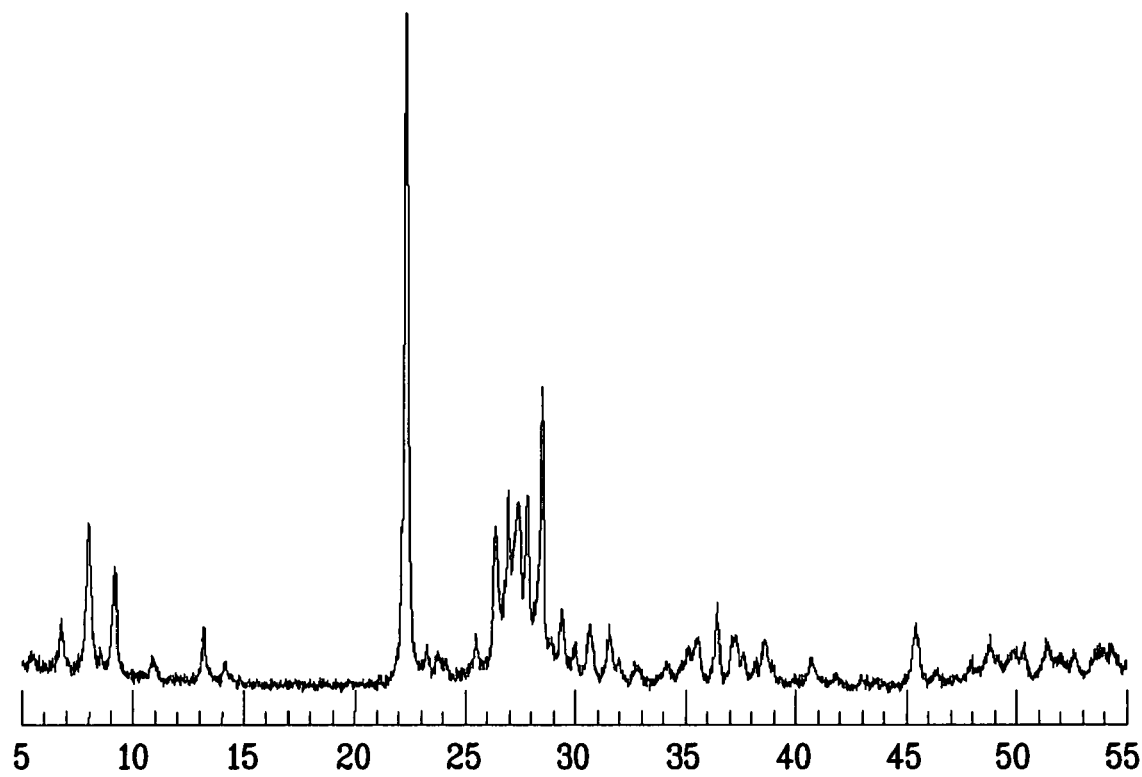
FIG. 9 is an X-ray diffraction pattern for the catalyst sample of Example 5B.

The catalyst precursor MoVNbTeSbOx prepared following the procedures above was placed in a crucible and placed in a furnace. A stream of CO$_2$ (50 cc/min) was flowing through the furnace and the temperature was raised to 600° C. at 2° C./min and held at 600° C. for 2 hr. The X-ray diffraction pattern for the catalyst sample thus obtained is presented in FIG. 9.

Example 6

Preparation of MoVNbTeSbOx Catalyst

Figure 10:
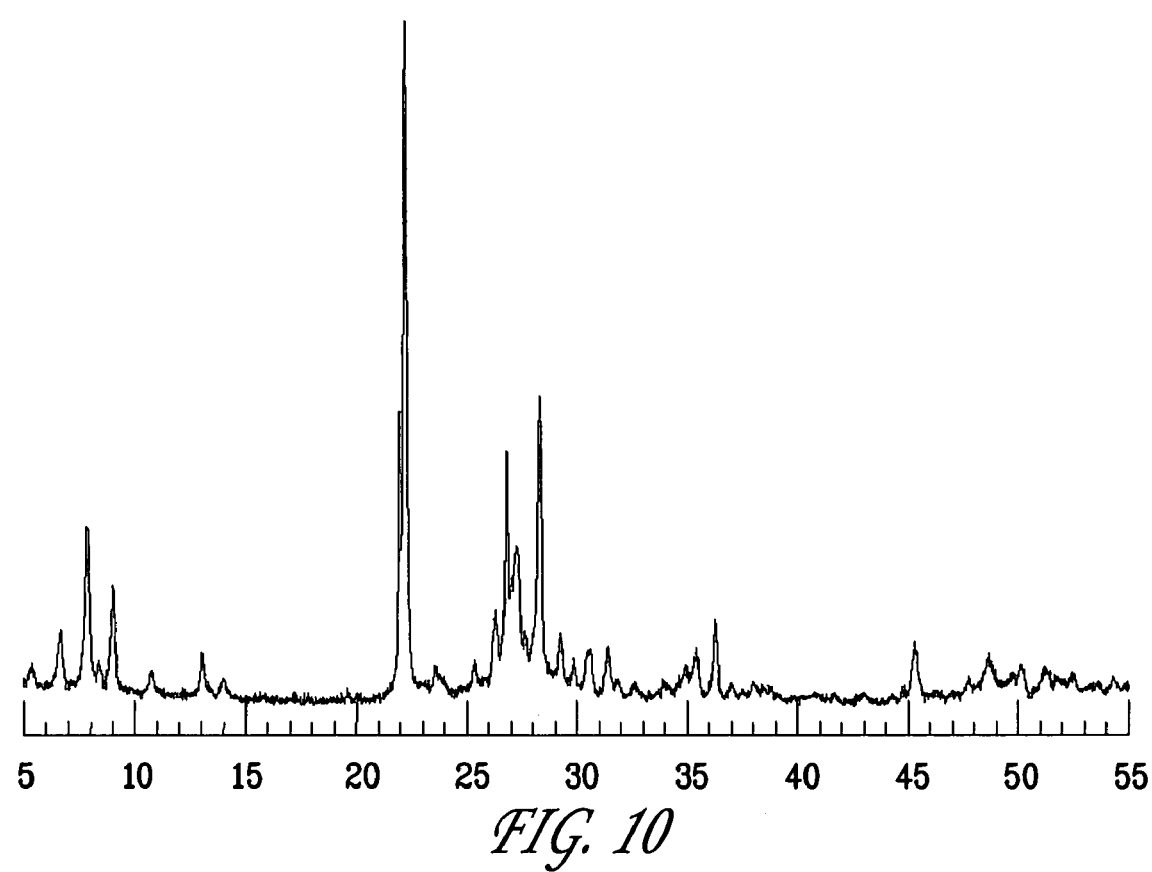
FIG. 10 is an X-ray diffraction pattern for the catalyst sample of Example 6.

To 900 grams of distilled water, 7.5 grams of ammonium metavanadate (NH$_4$VO$_3$), 52 grams of ammonium heptamolybdate tetrahydrate [(NH$_4$)$_6$Mo$_7$O$_{24}$.4H$_2$O], 15.5 grams of telluric acid [Te(OH)$_6$], and 4.5 grams of antimony chloride (SbCl$_3$) were added with stirring. Then 18.6 grams of niobium oxalate [Nb(HC$_2$O$_4$)$_5$] were dissolved in 200 grams of distilled water and then added to the above solution. After stirring the solution for one hour, the solution is then rotovaped to dryness at 50° C. with vacuum. A portion of the solid isolated was placed in a crucible and placed in a furnace. A stream of N$_2$ (50 cc/min) was flowing through the furnace and the temperature was raised to 600° C. at 2° C./min and held at 600° C. for 2 hr. The X-ray diffraction pattern for the catalyst sample thus obtained is presented in FIG. 10. The elemental analyses were: V—4.75 weight %, Nb—6.18%, Mo—44.85%, Te—9.52%, and Sb—2.9%.

Example 7

Preparation of MoVNbTeSbOx Catalyst

Figure 11:
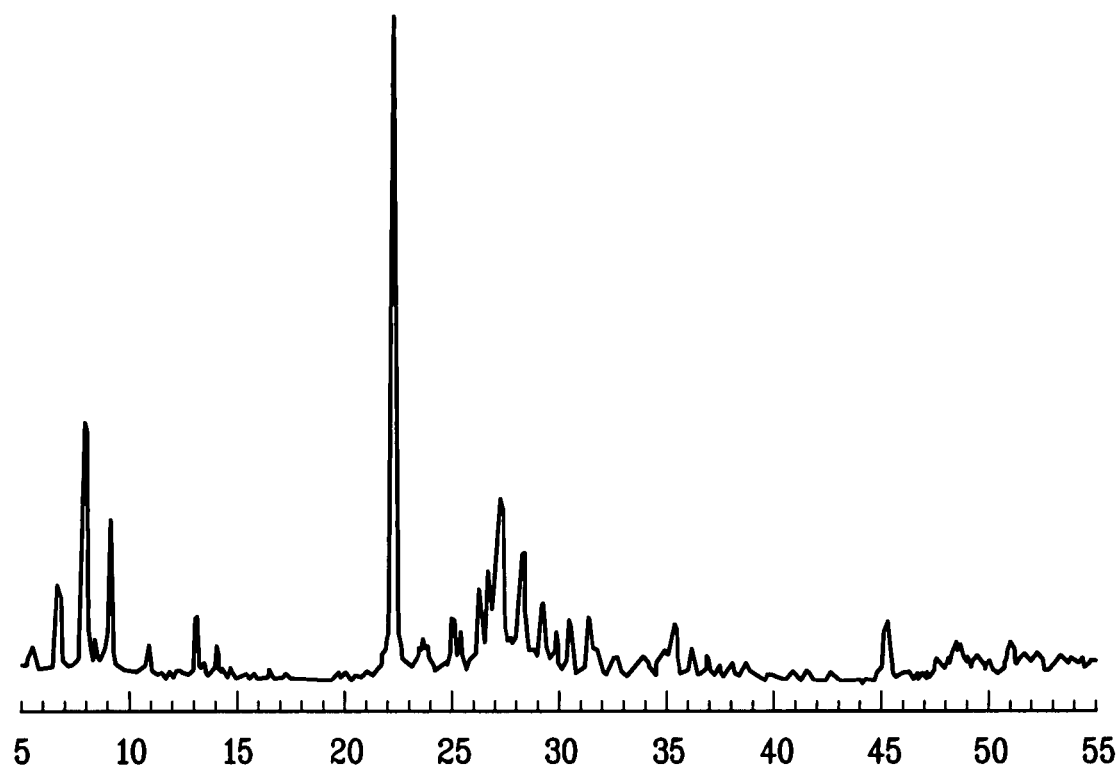
FIG. 11 is an X-ray diffraction pattern for the catalyst sample of Example 7.

In solution A, ninety grams of distilled water, 24.1 grams of ammonium heptamolybdate [(NH$_4$)$_6$Mo$_7$O$_{24}$.4H$_2$O], 3.9 grams of telluric acid [Te(OH)$_6$], and 0.9 grams of antimony chloride (SbCl$_3$) were combined in order with stirring. In solution B, 45 grams of distilled water was combined with stirring with 10.7 grams of vanadylsulfate hydrate (VOSO$_4$.nH$_2$O) with stirring. Finally, in solution C, 45 grams of distilled water was combined with 10.5 grams of niobium oxalate [Nb(HC$_2$O$_4$)$_5$] with stirring. Solution B was added to solution A. After 5 minutes of stirring, solution C was added to the mixed phase. The total preparation was then placed in a Teflon liner and put into a 300-mL autoclave. The autoclave was heated to 175° C. and maintained at that temperature for 48 hours. The autoclave was then cooled and the product filtered, washed with distilled water, and dried overnight. A portion of the solid isolated was placed in a crucible and placed in a furnace. A stream of N$_2$ (50 cc/min) was flowing through the furnace and the temperature was raised to 600° C. at 2° C./min and held at 600° C. for 2 hr. The X-ray diffraction pattern for the catalyst sample thus obtained is presented in FIG. 11.

Example 8

Figure 12:
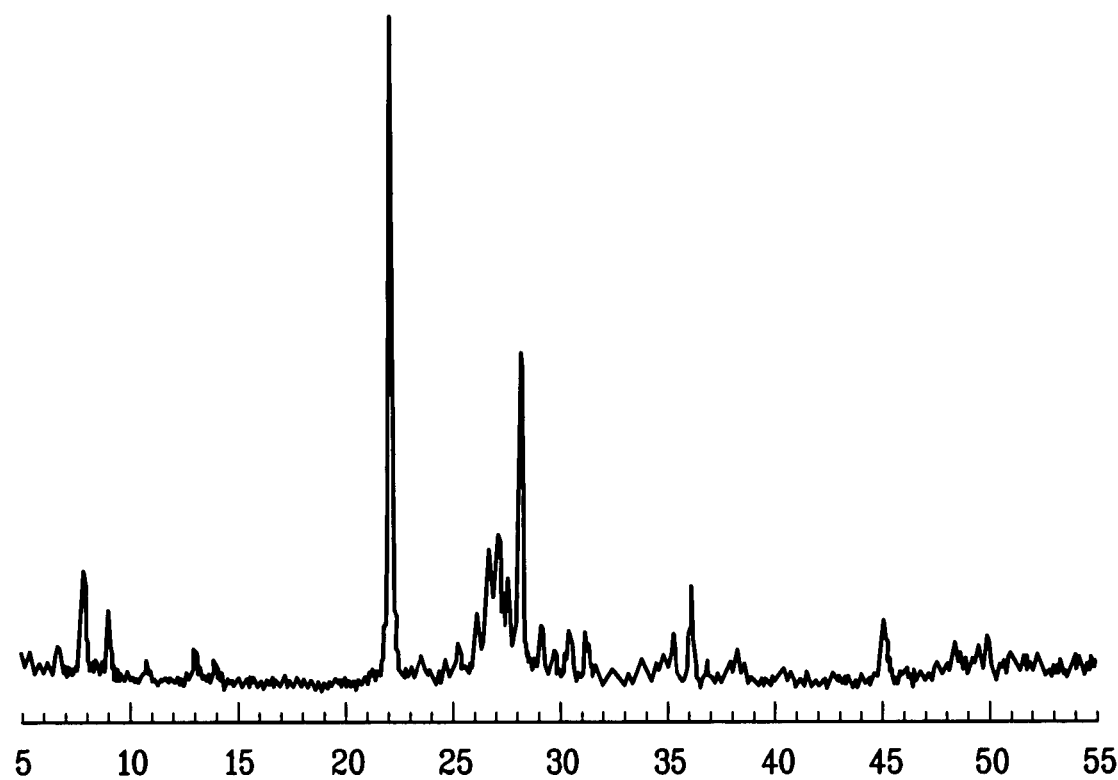
FIG. 12 is an X-ray diffraction pattern for the catalyst sample of Example 8.

To 700 grams of distilled water, 7.5 grams of ammonium metavanadate (NH$_4$VO$_3$), 52 grams of ammonium heptamolybdate tetrahydrate [(NH$_4$)$_6$Mo$_7$O$_{24}$.4H$_2$O], 15.5 grams of telluric acid [Te(OH)$_6$], and 4.5 grams of antimony chloride (SbCl$_3$) were added with stirring. Then 18.6 grams of niobium oxalate [Nb(HC$_2$O$_4$)$_5$] dissolved in 200 grams of distilled water was then added to the above solution. After stirring the solution for one hour, the solution is then rotovaped to dryness at 50° C. with vacuum. A portion of the preparation is then calcined in flowing nitrogen at 600° C. for 2 hours. The X-ray diffraction pattern for the catalyst sample thus obtained is presented in FIG. 12. The elemental analyses were: V—4.65 weight %, Nb—5.88%, Mo—44.28%, Te—10.7%, and Sb—2.82%.

Example 9

NH$_3$ Uptake Measurement

In one form, the active metal oxides disclosed herein exhibit acidity as determined by the chemisorption of NH$_3$ over these metal oxide materials. NH$_3$, a strong base, is titrated to indicate the acidic sites on the material. Many factors determine the actual amount of chemisorption such as surface area of the material, which is often significantly affected by the metal oxide preparation method, the temperature at which the chemisorption is tested, and the pressure at which the chemisorption is tested. The chemisorption of NH$_3$ per gram (mmole/g) of metal oxide was observed to be inversely proportional to the selectivity of acrylic acid production, as may be seen in Table 1 and FIGS. 13 and 14; while no such correlation was observed for the comparative VMoNbTe systems. As demonstrated, the lower the acidity, as measured by ammonia adsorption, the more selective the catalyst.

Tests to determine the chemisorption of NH$_3$ per gram of metal oxide were conducted using a Mettler TGA/SDTA 851 thermogravimetric analysis system at ambient pressure. The metal oxide sample was calcined in flowing helium to about 100° C. for about one hour; at least until a constant sample weight was obtained. Next, the sample was allowed to equilibrate in flowing helium and weighed. Chemisorption of ammonia was measured at 100° C. After being weighed, the sample was subjected to a number of pulses (about 12 seconds/pulse) of a gaseous mixture containing helium and ammonia until a constant weight was obtained. The gas mixture contained about 10 weight percent ammonia with the remainder being helium. After each pulse of the gas mixture being tested, the metal oxide sample was flushed with flowing helium for about 3 minutes. About 20 separate pulses of the gas mixture were used in each test. The increase in weight of the sample in terms of mg/g metal oxide based on the metal oxide sample weight after calcination was used to determine the mmoles of $NH_3$ adsorbed per gram of metal oxide.

TABLE 1

NH3 Uptake (mmole/g) and Catalytic Performance for the Mixed Metal Oxides Catalysts

| Example | $NH_3$ uptake (mmole/g) | Propane Conversion (%) | Acrylic Acid Selectivity (%) | Acetic Acid Selectivity (%) |
|---|---|---|---|---|
| 1A | 0.047 | 38 | 60 | 8 |
| 1B | 0.049 | 54 | 34 | 14 |
| 1C | 0.05 | 40 | 60 | 8 |
| 1D | 0.041 | 15 | 46 | 11 |
| 2 | 0.075 | 48 | 47 | 14 |
| 3 | 0.043 | 50 | 52 | 11 |
| 4 | 0.075 | 45 | 35 | 24 |
| 5A | 0.038 | 50 | 70 | 7 |
| 5B | 0.049 | 60 | 51 | 11 |
| 6 | 0.053 | 60 | 70 | 11 |
| 7 | 0.099 | 59 | 23 | 26 |

Example 10

Propane Oxidation to Acrylic Acid Using the MMOx Catalysts

The reactor used in the experiments is Hastlloy C with dimensions of 22 in. long×⅜ in. O.D.×0.035 in wall thickness. A piece of 8¾ in long×¼ in O.D. stainless steel tubing was used at the bottom of the reactor as a spacer to position and support the catalyst in the isothermal zone of the furnace. A ¼ in plug of glass wool was placed at the top of the spacer to keep the catalyst in place. A ⅛ in thermo-well was used in the catalyst bed, long enough to accommodate temperature scanning throughout the catalyst bed.

The catalyst was pressed into pellets then crushed and sized to 20-40 US sieve mesh. Typically 3 cc of the catalyst pre-sized to 20 to 40 mesh was diluted with 1 cc of quartz chips of the same size. The mixed portion of catalyst was then loaded into the reactor from the top. The catalyst bed typically was 12 cm in length. A ¼ in plug of glass wool was placed at the top of the catalyst bed to separate quartz chips from the catalyst. The remaining space at the top of the reactor was filled with quartz chips. The reactor was installed in the furnace with the catalyst bed in the middle of the furnace at the pre-marked isothermal zone. The reactor was then pressure and leak tested typically at 300 psig. A research control valve was used to control the reactor pressure typically at 50 psig. A 500 cc Isco syringe pump was used to introduce water to a vaporizer then through heated lines to the reactor; and Brooks mass flow controllers were used for other feed measurements. A research control valve was used to control the reactor pressure typically at 50 psig.

The catalyst was pre-conditioned in situ; heated to 200° C. with nitrogen flow at 150 cc/min. the reactor was then heated to 380° C. then the feed was introduced. A feed mixture containing propane/oxygen/nitrogen/water in the ratio of 5/9/69/17 was passed through the catalyst bed held at the reaction temperature at a GHSV of 2672 $h^{-1}$ and a pressure of 50 psi. The products exiting the reactor through heated lines routed to a Hewlett and Packard 5890 gas chromatograph with FID and TCD detectors for analysis. A J&W Scientific DB-1 capillary column 60 m×0.32 mm×1.0 micron film thickness was used for the analysis of hydrocarbon products. A Supelco 30 m×⅛ in stainless steel, Haysep DB column was used for water and other light gas analysis. Analyses were taken typically at a three-hour interval.

The GC analysis ramp program was set to: −30° C. for 3 min; 5° C./min to 120° C., held 0 min; 20° C./min to 200° C., held 22 min; and 30° C./min to 270° C. held to the end; with the total analysis time being 75 min.

Figure 15:
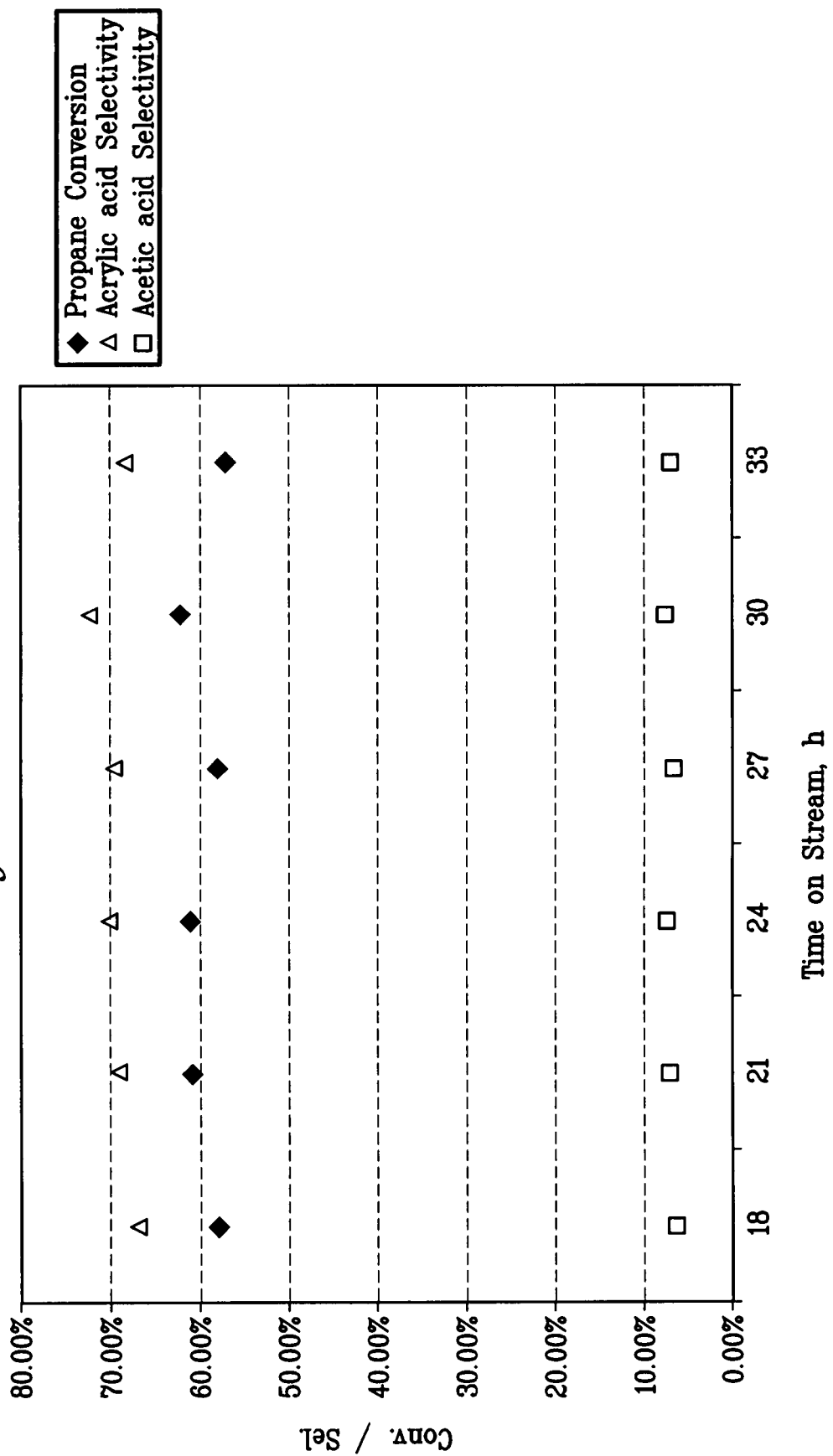
FIG. 15 is a plot of time-on-stream profile for propane oxidation to acrylic acid using the MoVNbTeSbOx catalyst for the catalyst sample of Example 6.
Figure 16:
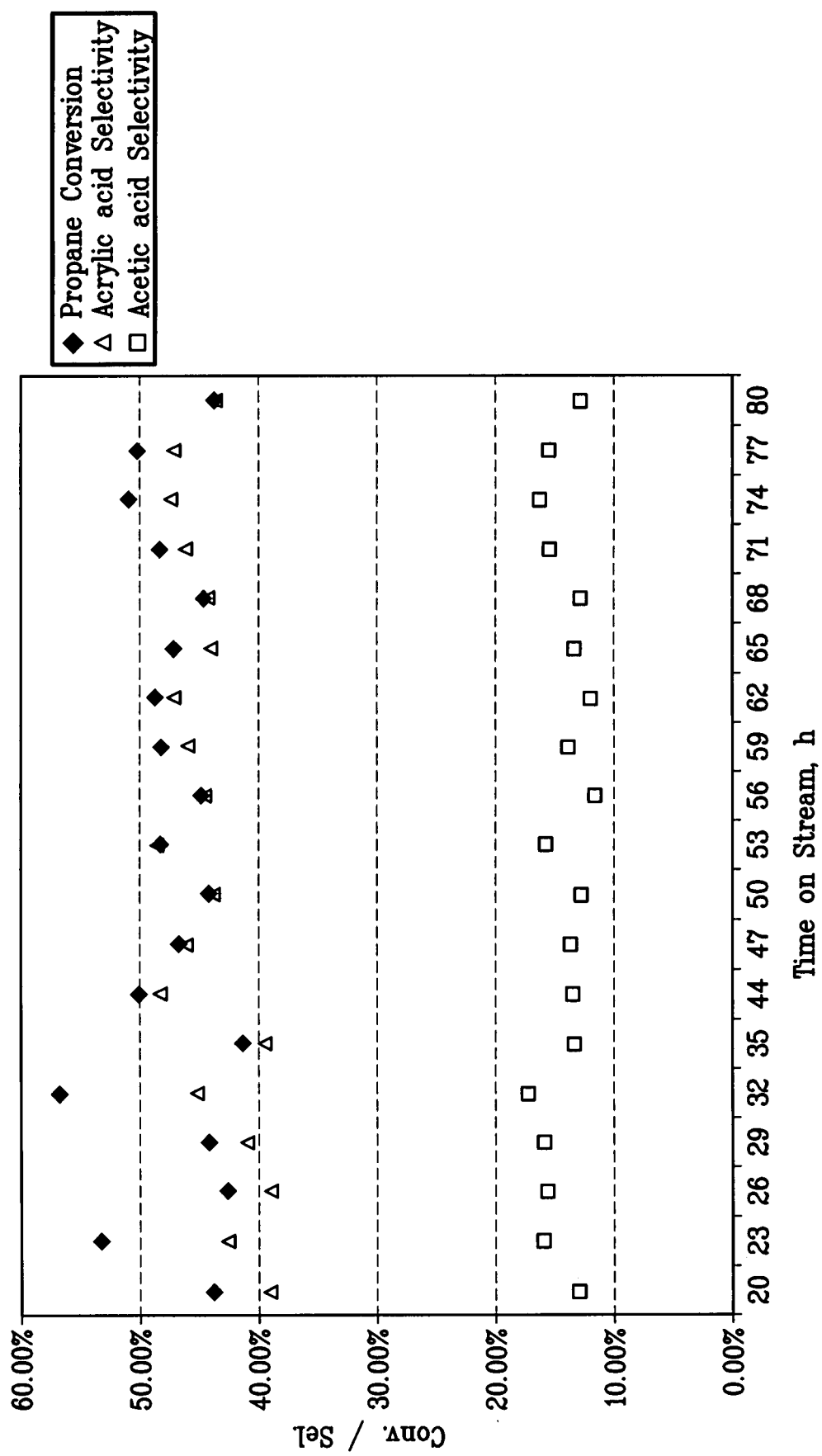
FIG. 16 is a plot of time-on-stream profile for propane oxidation to acrylic acid using the MoVNbTeOx catalyst for the catalyst sample of Example 2.

A typical time-on-stream (TOS) profile is presented for the catalyst system of Example 6 in FIG. 15. For comparison, a TOS profile for the comparative system of Example 6 is presented in FIG. 16. Results for catalysts with various compositions are shown in Table 2. Clearly the addition of Sb to the VMoNbTe mixed oxides system significantly increases the yield of acrylic acid.

TABLE 2

Selective Oxidation of Propane to Acrylic Acid
(50 psi, 380° C., GHSV = 2672 $h^{-1}$, Propane/$O_2$/$N_2$/$H_2O$ = 5/9/69/17)

| Example | Catalyst Composition | Propane Conversion (%) | Acrylic Acid Selectivity (%) | Acetic Acid Selectivity (%) |
|---|---|---|---|---|
| 1A | $V_{0.116}Mo_{0.641}Te_{0.164}Nb_{0.079}$ | 38 | 60 | 8 |
| 1B | $V_{0.119}Mo_{0.635}Te_{0.169}Nb_{0.077}$ | 54 | 34 | 14 |
| 1C | $V_{0.124}Mo_{0.632}Te_{0.155}Nb_{0.089}$ | 40 | 60 | 8 |
| 1D | $V_{0.119}Mo_{0.677}Te_{0.17}Nb_{0.087}$ | 15 | 46 | 11 |
| 2 | $V_{0.124}Mo_{0.648}Te_{0.143}Nb_{0.085}$ | 48 | 47 | 14 |
| 3 | $V_{0.128}Mo_{0.637}Te_{0.123}Nb_{0.083}Sb_{0.03}$ | 50 | 52 | 11 |
| 4 | $V_{0.134}Mo_{0.67}Te_{0.073}Nb_{0.089}Sb_{0.035}$ | 45 | 35 | 24 |
| 5A | $V_{0.13}Mo_{0.55}Te_{0.15}Nb_{0.12}Sb_{0.05}$ | 50 | 70 | 7 |
| 5B | $V_{0.147}Mo_{0.679}Te_{0.088}Nb_{0.086}Sb_0$ | 60 | 51 | 11 |
| 6 | $V_{0.128}Mo_{0.645}Te_{0.103}Nb_{0.092}Sb_{0.033}$ | 60 | 70 | 11 |
| 7 | $V_{0.123}Mo_{0.666}Te_{0.112}Nb_{0.08}Sb_{0.019}$ | 59 | 23 | 26 |
| 8 | $V_{0.13}Mo_{0.64}Te_{0.12}Nb_{0.09}Sb_{0.03}$ | 45 | 71 | 7 |

Example 11

Isolation of the Working Catalyst (Comparative)

Figure 17:
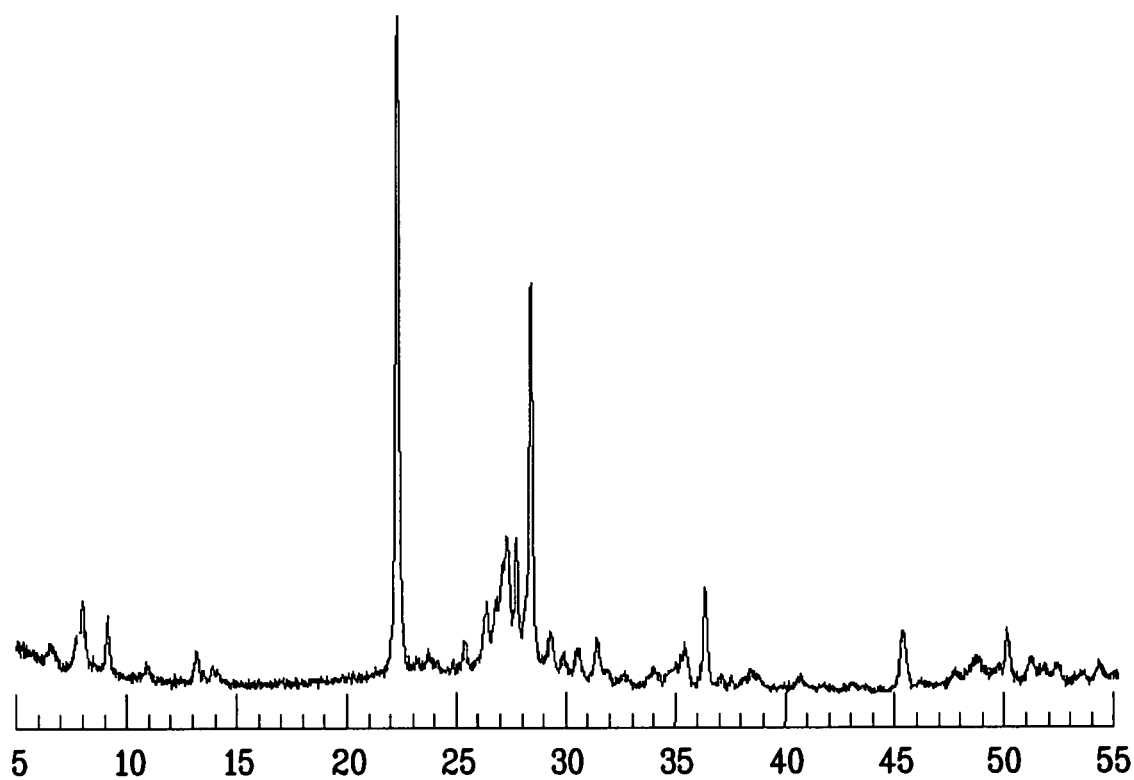
FIG. 17 is an X-ray diffraction pattern for the catalyst sample of Example 11.

The catalyst of Example 1A was tested for propane oxidation following the conditions in Example 10 for ca. 80 hr, after which the feed was switched off and the reactor was allowed to cool off under an $N_2$ flow (150 cc/min). The working catalyst was then separated from quartz and used for X-ray diffraction and other analyses. The X-ray diffraction pattern for the catalyst sample thus obtained is presented in FIG. 17.

Example 12

Isolation of the Working Catalyst

Figure 18:
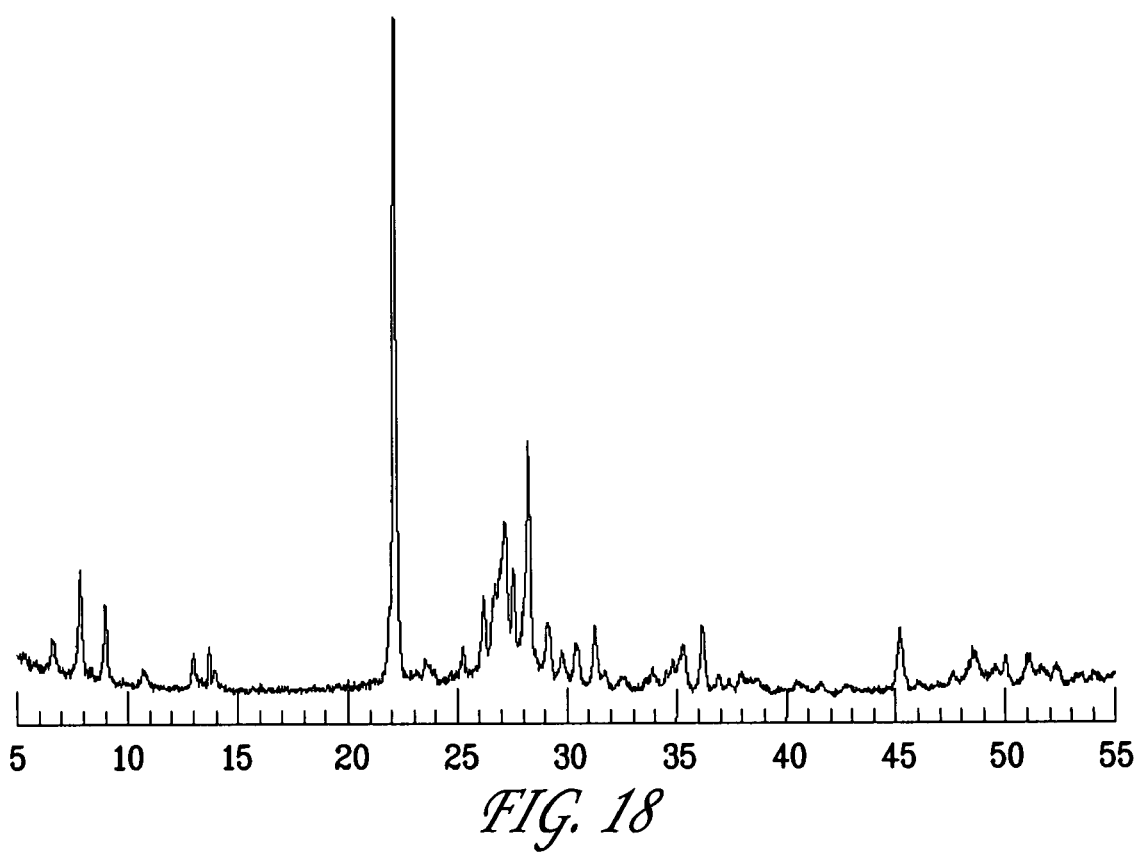
FIG. 18 is an X-ray diffraction pattern for the catalyst sample of Example 12.
Figure 19:
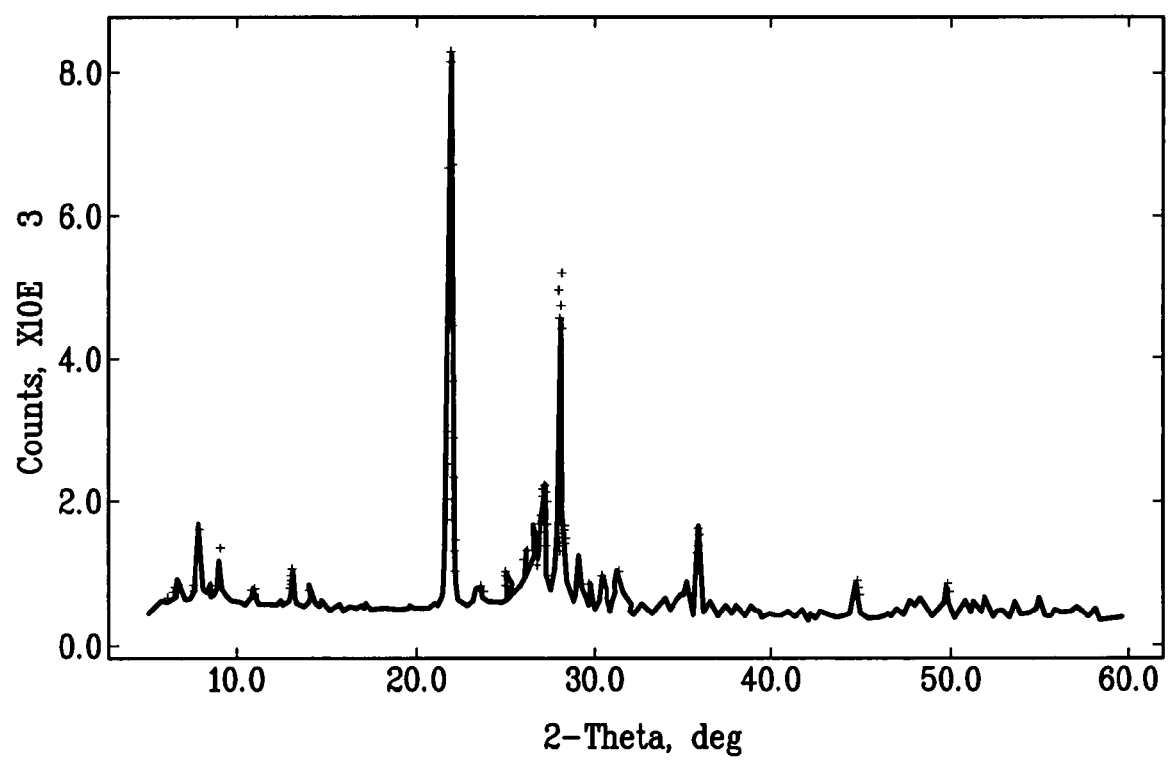
FIG. 19 is a profile fit for a catalyst consisting of three phases.

The catalyst of Example 3 was tested for propane oxidation following the conditions in Example 10 for ca. 80 hr, after which the feed was switched off and the reactor was allowed to cool off under an $N_2$ flow (150 cc/min). The working catalyst was then separated from quartz and used for X-ray diffraction and other analyses. The X-ray diffraction pattern for the catalyst sample thus obtained is presented in FIG. 18.

Example 13

Phase Analysis Using Powder X-Ray Diffraction Techniques

1. Data Acquisition

The X-ray diffraction data referred to herein were collected with a Scintag powder X-Ray Diffractometer, in a Bragg-Brentano configuration and equipped with a Peltier-cooled detector, using copper K-alpha radiation. The diffraction data were recorded by step-scanning at 0.01 to 0.02 degrees of two-theta, where theta is the Bragg angle, and count rate of two seconds per step.

2. Definition of Phases

"M1" Phase: Calculated Powder X-ray diffraction trace based on crystallographic data (space-group, unit cell and atom parameters) reported by P. DeSanto, D. J. Buttrey, R. K Grasselli, C. G. Lugmair, A. F. Volpe, B. H. Toby, and T. Vogt, Z. Kristallogr, 219, (2004) 152-165, Table 2.

"M2" Phase: Calculated Powder X-ray diffraction trace based on crystallographic data (space-group, unit cell and atom parameters) reported by P. DeSanto, D. J. Buttrey, R. K Grasselli, C. G. Lugmair, A. F. Volpe, B. H. Toby, and T. Vogt, Z. Kristallogr, 219, (2004) 152-165, Table 3.

"$TeMo_5O_{16}$" Phase: Calculated Powder X-ray diffraction trace based on crystallographic data (space-group, $P2_1/c$) reported by Y. Arnaud and J. Guidot, Acta Crystallogr, B33 (1977) 2151-2155, Table 1.

"$Te^{(O)}$" Phase: Calculated Powder X-ray diffraction trace based on crystallographic data reported by N. Bouad, L. Chapon, R. M. Marin-Ayral, F. Bouree-Vigneron, F. and J. C. Tedenac, J. C, Journal of Solid State Chemistry, 173 (2003) 189-195, as reported in the Inorganic Crystal Structure Database (ICSD), No. 96502.

"$NbTe_4$" Calculated Powder X-ray diffraction trace based on crystallographic data reported by S. van Smaalen, K. D. Bronsema and J. Mahy, Acta Crystallographica B, (1986) 42, 43-50, ICSD No. 61113.

"$MoO_2$" Calculated Powder X-ray diffraction trace based on crystallographic data reported by A. A. Bolzan, B. J. Kennedy, and C. J. Howard, Australian Journal of Chemistry, (1995) 48, 1473-1477, ICSD No. 80830.

3. Phase Analysis in GSAS

Rietveld refinement was performed using GSAS: General Structure Analysis System, Allen C. Larson & Robert B. Von Dreele, LANSCE, MS-H805, Los Alamos National Laboratory, Los Alamos, N.M. 87545 (2000).

An over-all zero shift parameter is refined as well as phase-specific parameters such as Unit Cell parameters, profile parameters, orientation, and phase fraction scale $S_{ph}$.

The full profile analysis is performed using the [5-60] 2 Theta range.

A quantitative phase analysis (wt. fraction) is possible in GSAS as follows (from the GSAS Manual), where the wt. fraction (or wt. %, which is wt. fraction×100) of each phase can be determined:

The phase fraction scale, $S_{ph}$, is applied only to reflections from the p-th phase. These can be used for quantitative phase analysis for powder mixtures.

The $S_{ph}$ scale factors are proportional to the unit cell composition of the sample.

They can be converted to, for example, weight fractions, $W_p$, by:

$$W_p = \frac{S_{ph}m_p}{\sum_{p=1}^{N_p} S_{ph}m_p}$$

Where $m_p$ is the unit cell mass for phase p. The weight fractions for multiphase mixtures are automatically computed during the least-squares refinement. The unit cell mass, $m_p$, for each phase is computed from the atom site multiplicities and fractions present for that phase.

A profile fit of a catalyst sample consisting of three phases is shown below

|  | Phase | | |
| --- | --- | --- | --- |
|  | M1 | M2 | $TeMo_5O_{16}$ |
| Wt Fraction | 0.672 | 0.274 | 0.054 |

Example 14

Phase Analyses for MoVNbTeOx and MoVNbTeSbOx Systems

The X-ray diffraction patterns for the MoVNbTeOx (comparative) system and the MoVNbTeSbOx system are shown in FIGS. 4-9. The catalysts generally contain multiple phases and the phase composition was analyzed using the techniques described above. Detailed phase compositions are listed in Table 2.

TABLE 3

Phase Composition of The Mixed Metal Oxide Catalysts

| Example | Catalyst Composition | M1 | M2 | $TeMo_5O_{16}$ | $NbTe_4$ | $Te^{(0)}$ |
|---|---|---|---|---|---|---|
| 1A, fresh | $V_{0.116}Mo_{0.641}Te_{0.164}Nb_{0.079}$ | 0.588 | 0.282 | 0.097 | | 0.032 |
| 11, working | | 0.678 | 0.278 | 0.006 | 0.001 | 0.036 |
| 3, fresh | $V_{0.128}Mo_{0.637}Te_{0.123}Nb_{0.083}Sb_{0.03}$ | 0.706 | 0.176 | 0.081 | | 0.037 |
| 12, working | | 0.782 | 0.174 | 0.023 | 0.005 | 0.016 |
| 1B | $V_{0.119}Mo_{0.635}Te_{0.169}Nb_{0.077}$ | 0.593 | 0.270 | 0.099 | | 0.038 |
| 1C | $V_{0.124}Mo_{0.632}Te_{0.155}Nb_{0.089}$ | 0.616 | 0.361 | | | 0.024 |
| 1D | $V_{0.119}Mo_{0.677}Te_{0.17}Nb_{0.087}$ | 0.968 | 0.031 | | | |
| 2 | $V_{0.124}Mo_{0.648}Te_{0.143}Nb_{0.085}$ | 0.726 | 0.183 | 0.045 | | 0.046 |
| 8 | $V_{0.13}Mo_{0.64}Te_{0.12}Nb_{0.09}Sb_{0.03}$ | 0.700 | 0.213 | 0.047 | | 0.039 |
| 4 | $V_{0.134}Mo_{0.67}Te_{0.073}Nb_{0.089}Sb_{0.035}$ | 0.65 | 0.297 | 0.052 | | |
| 5A | $V_{0.13}Mo_{0.55}Te_{0.15}Nb_{0.12}Sb_{0.05}$ | 0.757 | 0.155 | 0.050 | | 0.039 |
| 5B | $V_{0.147}Mo_{0.679}Te_{0.088}Nb_{0.086}Sb_{0}$ | 0.787 | 0.122 | 0.042 | | 0.048 |
| 6 | $V_{0.128}Mo_{0.645}Te_{0.103}Nb_{0.092}Sb_{0.033}$ | 0.772 | 0.182 | 0.036 | | 0.011 |
| 7 | $V_{0.123}Mo_{0.666}Te_{0.112}Nb_{0.08}Sb_{0.019}$ | 0.898 | 0.082 | 0.002 | | |

Example 15

Figure 20:
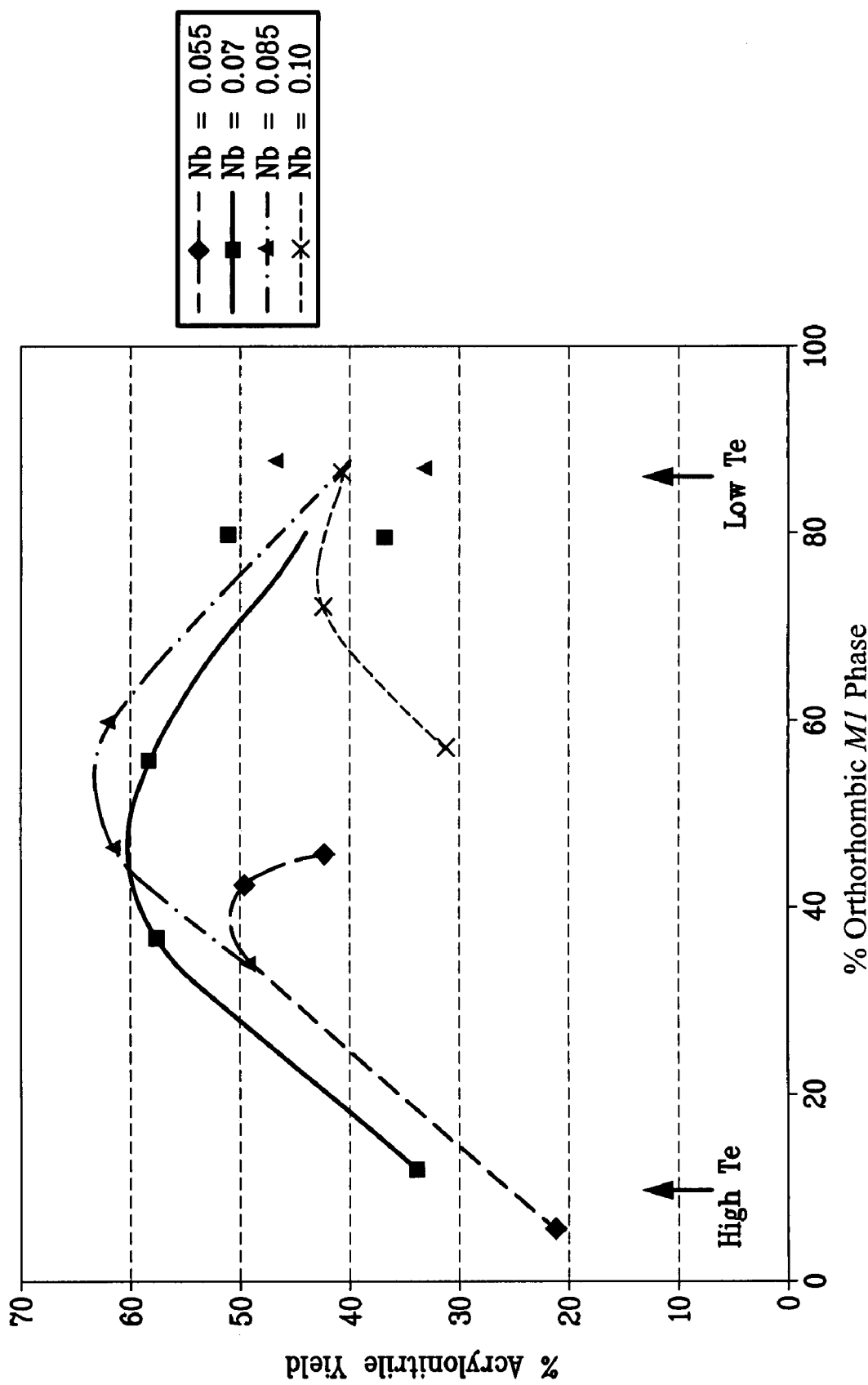
FIG. 20 is a plot of acrylonitrile yield vs. M1 phase fraction for MoVNbTeOx catalyzed propane ammoxidation to acrylonitrile.
Figure 21:
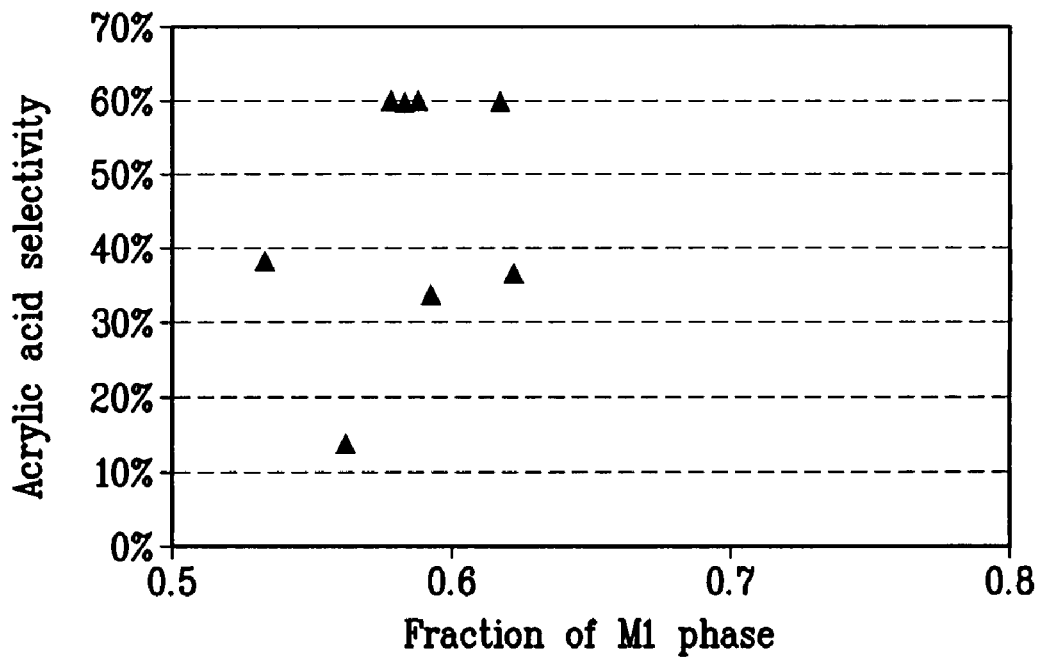
FIG. 21 is a plot of acrylic acid selectivity vs. fraction of M1 phase for the MoVNbTeOx comparative system.
Figure 22:
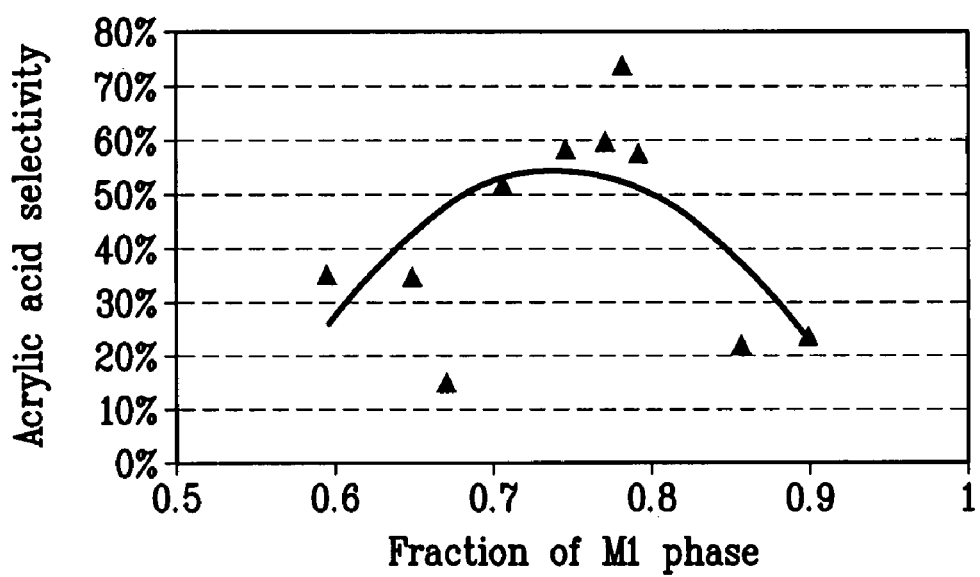
FIG. 22 is a plot of acrylic acid selectivity vs. fraction of M1 phase for the MoVNbTeSbOx system.

Comparison of the Optimal Phase Composition for the MoVNbTeOx (comparative) and the MoVNbTeSbOx Systems The phase compositions were varied systematically in both systems and their effects on acrylic acid selectivity were evaluated. Consistent with literature reports, propane ammoxidation to acrylonitrile is mechanistically similar to propane oxidation to acrylic acid, as shown in FIG. 20. The optimal phase composition for high acrylic acid selectivity in a MoVNbTeOx system for the M1 phase weight fraction is between 0.5 to 0.6, as shown in FIG. 21. For the MoVNbTeSbOx systems disclosed herein, the optimal phase composition for the M1 phase weight fraction is between 0.7 to 0.8, as shown in FIG. 22.

Clearly, the balance of M1 and M2 phases required for selective propane oxidation to acrylic acid is different with the addition of antimony. The optimal phase composition shifts from 40 to 60 wt. % M1 for a V—Mo—Ne—Te—O system (comparative) to 70 to 80 wt. % M1 for the V—Mo—Ne—Te—Sb—O system.

All patents, test procedures, and other documents cited herein, including priority documents, are fully incorporated by reference to the extent such disclosure is not inconsistent with the disclosure herein and for all jurisdictions in which such incorporation is permitted.

While the illustrative forms have been described with particularity, it will be understood that various other modifications will be apparent to and can be readily made by those skilled in the art without departing from the spirit and scope of applicants' disclosure. Accordingly, it is not intended that the scope of the claims appended hereto be limited to the examples and descriptions set forth herein but rather that the claims be construed as encompassing all the features of patentable novelty, including all features which would be treated as equivalents thereof by those skilled in the relevant art.

What is claimed is:

1. A process for preparing a catalyst for the oxidation of an alkane, alkene or mixtures thereof, the process comprising the steps of:
   (a) admixing metal compounds, at least one of which is oxygen containing compound, and at least one solvent to form a solution;
   (b) removing the solvent from the solution to obtain a catalyst precursor; and
   (c) calcining the catalyst precursor at a temperature from 350° C. to 850° C. under an inert atmosphere to form a mixed-metal oxide catalyst having the formula

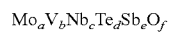

wherein, when a=1, b=0.01 to 1.0, c=0.01 to 1.0, d=0.01 to 1.0, e=0.01 to 1.0, and f is dependent upon the oxidation state of the other elements, said catalyst further characterized by having at least two crystal phases, the first crystal phase being an orthorhombic M1 phase and the second crystal phase being a pseudo-hexagonal M2 phase, said orthorhombic M1 phase present in an amount between greater than 60 weight percent to less than 90 weight percent and wherein said catalyst exhibits a chemisorption of $NH_3$ of less than about 0.2 mmole per gram of metal oxide.

2. The process of claim 1, wherein said orthorhombic M1 phase is present in an amount between about 70 weight percent to about 80 weight percent.

3. The process of claim 2, wherein said pseudo-hexagonal M2 phase is present in an amount between about 20 weight percent to about 30 weight percent.

4. The process of claim 1, wherein said pseudo-hexagonal M2 phase is present in an amount between about 10 weight percent to about 30 weight percent.

5. The process of claim 4, wherein said catalyst is further characterized by having a $TeMo_5O_{16}$ phase, said $TeMo_5O_{16}$ phase present in an amount less than 10 weight percent.

6. The process of claim 3, wherein said catalyst is further characterized by having a $TeMo_5O_{16}$ phase, said $TeMo_5O_{16}$ phase present in an amount less than 10 weight percent.

7. The process of claim 1, wherein said catalyst is further characterized by having a $TeMo_5O_{16}$ phase, said $TeMo_5O_{16}$ phase present in an amount less than 10 weight percent.

8. A catalyst for the oxidation of an alkane, alkene or mixtures thereof, said catalyst comprising a mixed-metal oxide having the formula:

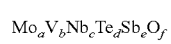

wherein, when a=1, b=0.01 to 1.0, c=0.01 to 1.0, d=0.01 to 1.0, e=0.01 to 1.0, and f is dependent upon the oxidation state of the other elements, and wherein said catalyst exhibits a chemisorption of $NH_3$ of less than about 0.2 mmole per gram of metal oxide.

9. The catalyst of claim 8, wherein said catalyst exhibits a chemisorption of $NH_3$ of less than about 0.1 mmole per gram of metal oxide.

10. The catalyst of claim 8, wherein said catalyst further characterized by having at least two crystal phases, the first crystal phase being an orthorhombic M1 phase and the second crystal phase being a pseudo-hexagonal M2 phase, said orthorhombic M1 phase present in an amount between greater than 60 weight percent to less than 90 weight percent.

11. The catalyst of claim 10, wherein said orthorhombic M1 phase is present in an amount between about 70 weight percent to about 80 weight percent.

12. The catalyst of claim 11, wherein said pseudo-hexagonal M2 phase is present in an amount between about 20 weight percent to about 30 weight percent.

13. The catalyst of claim 10, wherein said pseudo-hexagonal M2 phase is present in an amount between about 10 weight percent to about 30 weight percent.

14. The catalyst of claim 13, wherein said catalyst is further characterized by having a $TeMo_5O_{16}$ phase, said $TeMo_5O_{16}$ phase present in an amount less than 10 weight percent.

15. The catalyst of claim 12, wherein said catalyst is further characterized by having a $TeMo_5O_{16}$ phase, said $TeMo_5O_{16}$ phase present in an amount less than 10 percent.

16. The catalyst of claim 10, wherein said catalyst is further characterized by having a $TeMo_5O_{16}$ phase, said $TeMo_5O_{16}$ phase present in an amount less than 10 weight percent.

17. The catalyst of claim 8, wherein the alkane is a $C_{1-8}$ alkane or mixtures thereof.

18. The catalyst of claim 8, wherein the alkene is a $C_{1-8}$ alkene or mixtures thereof.

19. The process of claim 1, wherein said catalyst exhibits a chemisorption of $NH_3$ of less than about 0.1 mmole per gram of metal oxide.

* * * * *